(12) United States Patent
Janes

(10) Patent No.: US 7,317,819 B2
(45) Date of Patent: Jan. 8, 2008

(54) APPARATUS AND METHOD FOR THREE-DIMENSIONAL IMAGING

(75) Inventor: Dean Norman Janes, Burbank, CA (US)

(73) Assignee: Imaging3, Inc., Burbank, CA (US)

( * ) Notice: Subject to any disclaimer, the term of this patent is extended or adjusted under 35 U.S.C. 154(b) by 731 days.

(21) Appl. No.: 10/872,951

(22) Filed: Jun. 21, 2004

(65) Prior Publication Data

US 2005/0020902 A1      Jan. 27, 2005

Related U.S. Application Data

(63) Continuation-in-part of application No. 10/229,889, filed on Aug. 28, 2002, now Pat. No. 6,754,297.

(51) Int. Cl.
*G06K 9/00* (2006.01)

(52) U.S. Cl. .......................... 382/128; 128/922; 378/4; 382/154

(58) Field of Classification Search ................ 382/128, 382/130, 131, 132, 154; 128/922; 378/4–27; 250/363.04
See application file for complete search history.

(56) References Cited

U.S. PATENT DOCUMENTS

| | | | | | |
|---|---|---|---|---|---|
| 5,023,894 | A | * | 6/1991 | Yamashita et al. | ............. 378/4 |
| 5,841,830 | A | * | 11/1998 | Barni et al. | .................... 378/15 |
| 5,920,395 | A | * | 7/1999 | Schulz | ....................... 356/622 |
| 6,125,163 | A | * | 9/2000 | Barth et al. | .................... 378/4 |
| 2002/0045817 | A1 | * | 4/2002 | Ichihashi | .................... 600/425 |
| 2004/0054248 | A1 | * | 3/2004 | Kimchy et al. | ................ 600/3 |

* cited by examiner

*Primary Examiner*—Bhavesh M Mehta
*Assistant Examiner*—Anand Bhatnagar
(74) *Attorney, Agent, or Firm*—Pillsbury Winthrop Shaw Pittman LLP

(57) ABSTRACT

A computing device in a three-dimensional imaging system utilizes a plurality of distance readings and reference readings from the at least one subject sensor to determine a subject location and a subject volume and establish a base-three dimensional map of a subject. A base-three dimensional map may be pre-existing. A plurality of two-dimensional image exposures along with a plurality of associated reference locations are created by utilizing an image source and an image receptor around an inner circumference of an imaging gantry. The plurality of two-dimensional image exposures is digitized to create a plurality of digital two-dimensional image exposures. The computing device receives the plurality of digital two-dimensional image exposures and the plurality of associated reference locations. The overlaying, interpolating, and pasting of the plurality of digital two-dimensional image exposures on the base three-dimensional map creates a base three-dimensional image exposure, which is displayed on a display device.

27 Claims, 18 Drawing Sheets

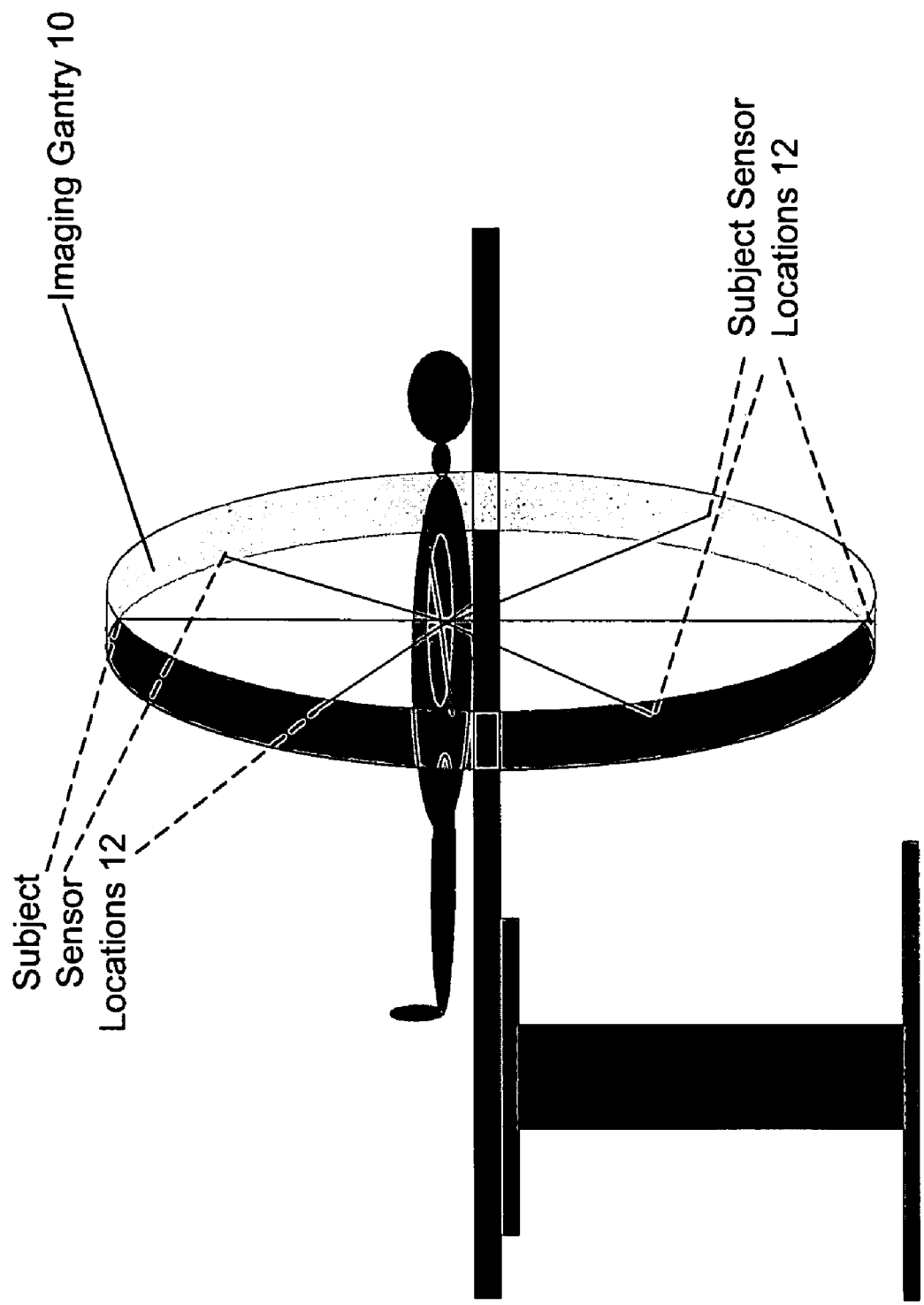

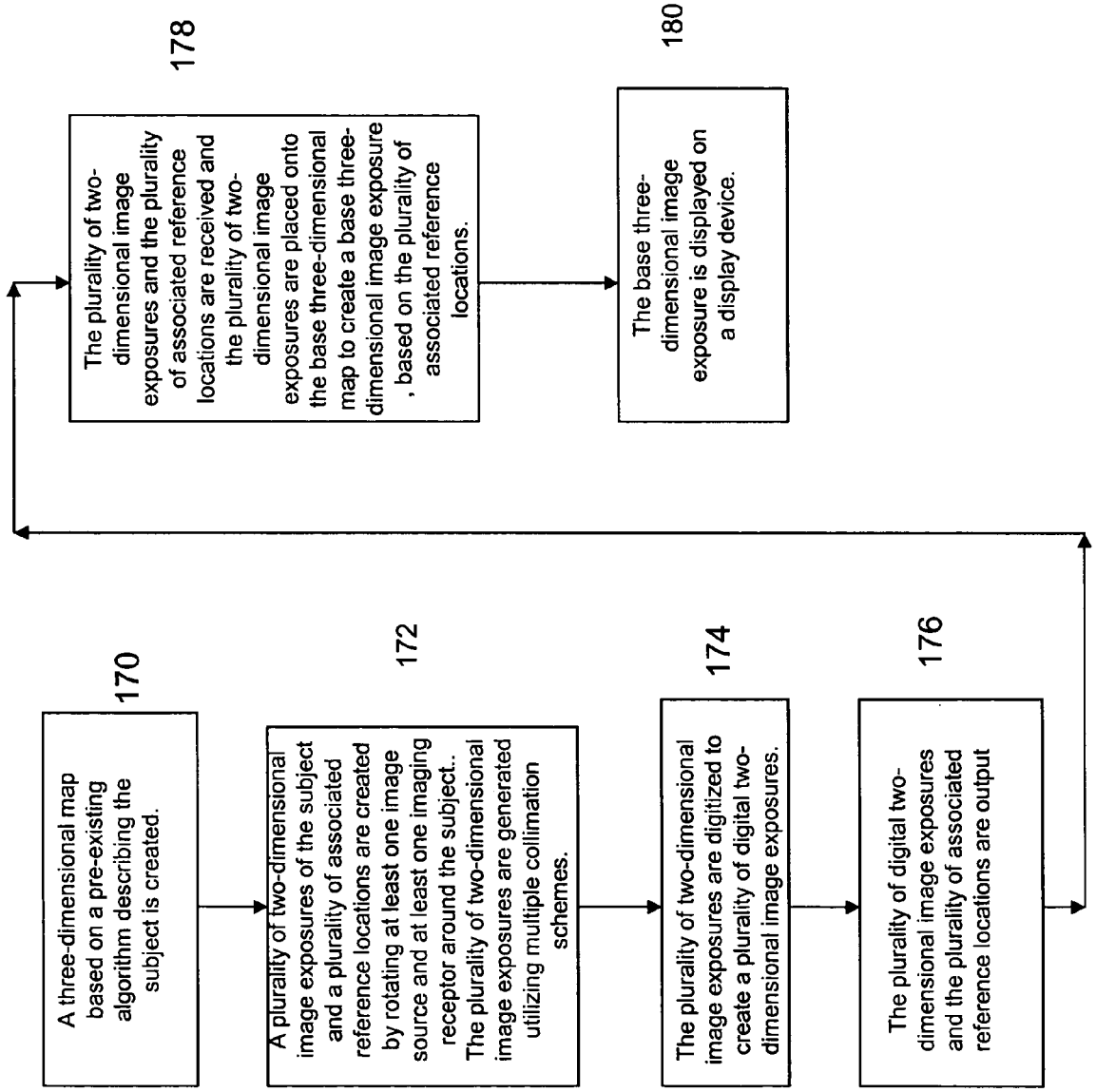

APPARATUS AND METHOD FOR THREE-DIMENSIONAL IMAGING

This application is a continuation-in-part application of application Ser. No. 10/229,889, filed Aug. 28, 2002 now U.S. Pat. No. 6,754,297, which application is hereby incorporated by reference in its entirety.

BACKGROUND

Medical imaging systems allow medical professionals to view a subject's internal features with minimal risk to the subject in terms of radiation exposure. Medical imaging systems image subjects by utilizing a variety of technologies such as Fluoroscopy, Computerized Tomography ("CT"), Magnetic Resonance Imaging (MRI), and Ultrasound. In CT scanning, a slice or tomographic slice is created by rotating an x-ray source and an image receptor partially or completely around a subject. Tomography utilizes a fulcrum reference, which is determined by adjusting the patient distance from the center of the perpendicularity of the x-ray source and x-ray receptor. The slice depth is determined by the distance of the subject from the center of the perpendicularity. A three-dimensional image of these slices can be constructed by compiling the images together as layers. Magnetic resonance imaging utilizes similar technology as a CT scanner except that a MRI device utilizes a magnetic field and radio signals to accomplish the tomographic planar image. The three-dimensional MRI images can be constructed from the MRI slice images. Ultrasound utilizes sound echoing technology to create a two-dimensional ultrasound image relative to a single plane in reference to the position of the ultrasound device and the angle the device is placed in reference to the subject being imaged. A three-dimensional ultrasound image can be reconstructed from the combination of the different two-dimensional ultrasound images.

Fluoroscopy systems utilize an image source, e.g., x-ray source, and an image receptor, to provide a real-time display of a two-dimensional fluoroscopic image in reference to a single plane, either AP (anterior/posterior) or any angle where the subject is perpendicular to the plane of the image source and image receptor. The image source and image receptor may be rotated partially around the patient, thus placing the image source and image receptor at different angles perpendicular to the patient, in order to create a plurality of two-dimensional fluoroscopic images.

For procedures such as angioplasty, where a device is placed inside an artery or vein and moves throughout the artery or vein, or pain management, where a needle is introduced into a specific area of the spine and it is desirable to view the exact area where the needle is introduced, a three-dimensional real-time or a three-dimensional continuously updatable imaging system may be desirable. In current systems utilizing MRI, CT, Ultrasound, or Fluoroscopy, three-dimensional (3D) images may be reconstructed from a plurality of two-dimensional images, however the reconstruction is normally done in post-processing, and not in real-time. In other words, it may take a few hours to completely scan or 360 scan the patient using other imaging technologies and even more time to construct or reconstruct a 3D image from the plurality of two-dimensional images. The 3D images are normally reference images that are later used for analysis by medical personnel. If the 3D image needs to be updated, e.g., to track the path of the angioplasty device through the artery or vein, a complete new 3D image would need to be created, meaning the entire area of the subject would need to be rescanned, which as mentioned before, can be a time-consuming process. Thus, it is desirable to be able to view only a specific subset of the scanned area or the complete 360 scanned area while the procedure is occurring, and to have this specific subset of the scanned area or the 360 scanned area be updated continuously or in real-time.

BRIEF DESCRIPTION OF THE DRAWINGS

FIG. 5a illustrates how a subject sensor maps patient depth within a gantry according to an embodiment of the invention;

FIG. 15 illustrates a creation of a three-dimensional image utilizing multiple collimation schemes according to an embodiment of the present invention.

DETAILED DESCRIPTION

Figure 1:
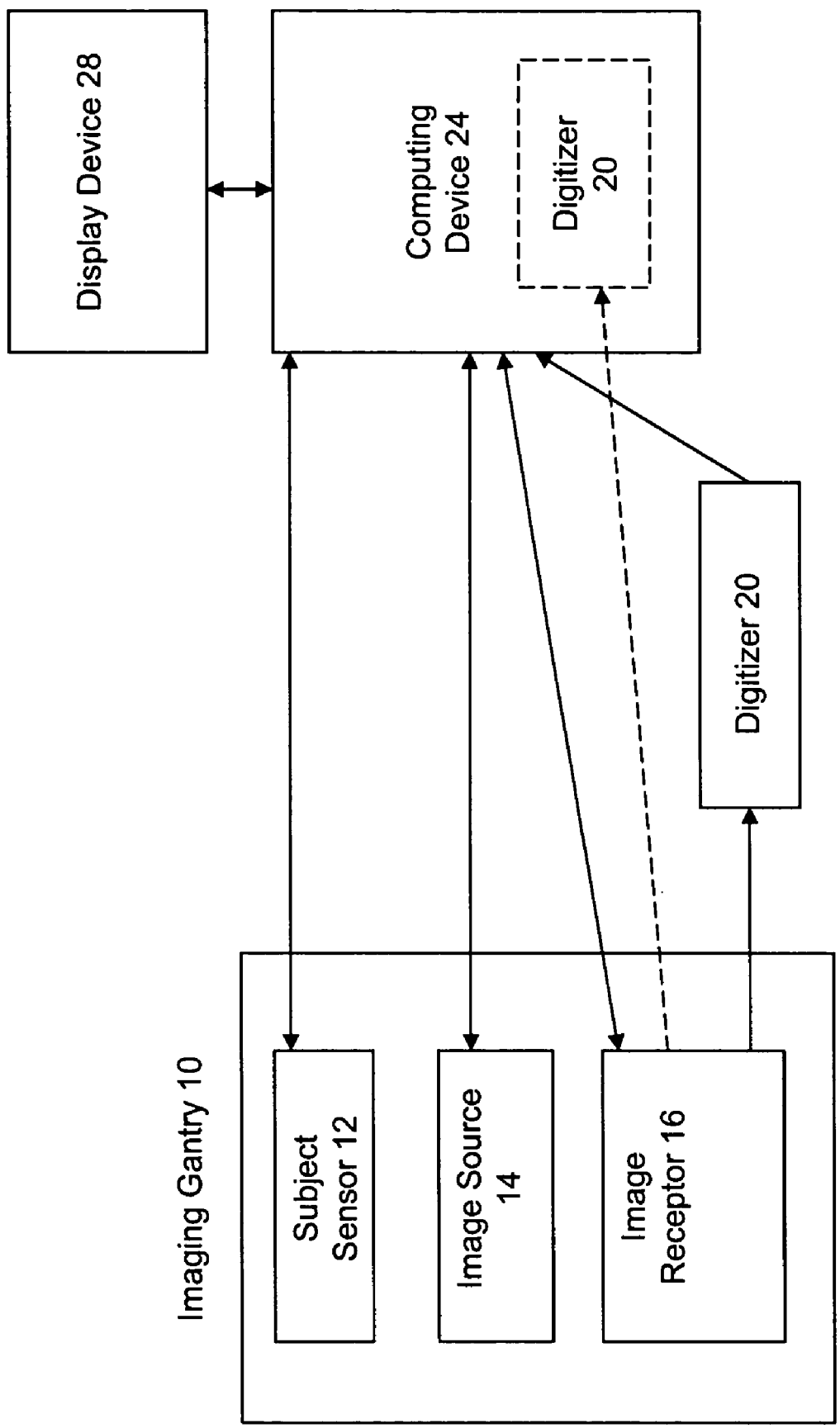
FIG. 1 illustrates a block diagram of a three-dimensional imaging system according to an embodiment of the present invention.

The present invention relates to an apparatus and a method for displaying three-dimensional image exposures of a subject. Image exposures may be fluorographic images, fluoroscopic images, radiographic images, or other similar images. The three-dimensional imaging system may utilize fluoroscopy technology to produce the three-dimensional images. The three-dimensional imaging system may include at least one subject sensor 12, at least one image source 14, at least one image receptor 16, an image digitizer 20, a computing device 24, and a display device 28. The at least one image source 14, the at least one image receptor 16, and the at least one subject sensor 12 may be located in an imaging gantry 10. The three-dimensional imaging system may include more than one subject sensor 12, image source 14, or image receptor 16. The image source 16 may be an x-ray source.

FIG. 1 illustrates a block diagram of a three-dimensional imaging system according to an embodiment of the present invention. In an embodiment of the invention, the computing device 24 of the three-dimensional imaging system may utilize a plurality of distance readings and reference readings from the at least one subject sensor 12 in the imaging gantry 10 to assist in establishing a base-three dimensional map of a subject. A plurality of two-dimensional image exposures along with a plurality of associated reference locations may be created by rotating the at least one image source 14 and the at least one image receptor 16 around an inner circumference of the imaging gantry 10.

In an embodiment of the invention, the computing device 24 of the three-dimensional imaging system may utilize a plurality of distance readings from the at least one subject sensor 12 in the imaging gantry to assist in establishing the base-three dimensional map of the subject. The computing device 24 may utilize geometry principles, algorithms, processes, memory functions, math functions, or any combination thereof, along with the distance readings, in order to produce a base three-dimensional map of the subject. Illustratively, the computing device may have predetermined positions that the at least one subject sensors may be at when capturing an image. Based on the predetermined or known positions, the computing device may not need to utilize any reference readings in creating the base three-dimensional image map. Instead, the computing device 24 may use the combination of an algorithm and a math function to create the base-three dimensional map, along with the distance readings. For general knowledge, reference readings are utilized to provide a location of the subject volume to be imaged in reference to the subject sensor and/or imaging gantry and their reference geometry In an embodiment of the invention, the computing device may not utilize distance readings or reference readings. Instead, a certain point on an object to be medically imaged may be placed in a specific location and based on previously calculated information, the computing device 24 may be able to create a base three-dimensional map. For example, a patient may have already been measured in order to determine width, height, and depth at a plurality of points. The patient may have his torso placed at a specific location in the three-dimensional imaging system and based on the previous measurements, a base three-dimensional map may be created for the subject. The base three-dimensional maps may be created in this fashion using an algorithm, geometry calculations, math functions, or a combination of the above-mentioned processes.

The plurality of two-dimensional image exposures may be digitized by a digitizer 20 to create a plurality of digital two-dimensional image exposures. The digitizer 20 may be a separate physical device. Alternatively, the digitizer 20 may be located in the computing device 24 (shown by dotted line in FIG. 1). The computing device 24 may receive the plurality of digital two-dimensional image exposures and the plurality of associated reference locations and may utilize the plurality of associated reference locations to identify where on the base three-dimensional map each of the plurality of digital two-dimensional image exposures are placed. The plurality of digital two-dimensional image exposures may be overlaid, pasted, or interpolated on the base three-dimensional map to create a base three-dimensional image exposure. In one embodiment of the invention utilizing interpolation, the plurality of digital two-dimensional image exposures may be interpolated onto the base three-dimensional map by using a math formulation or algorithm. The base three-dimensional image exposure may be transmitted from the computing device 24 to the display device 28.

Figure 2:
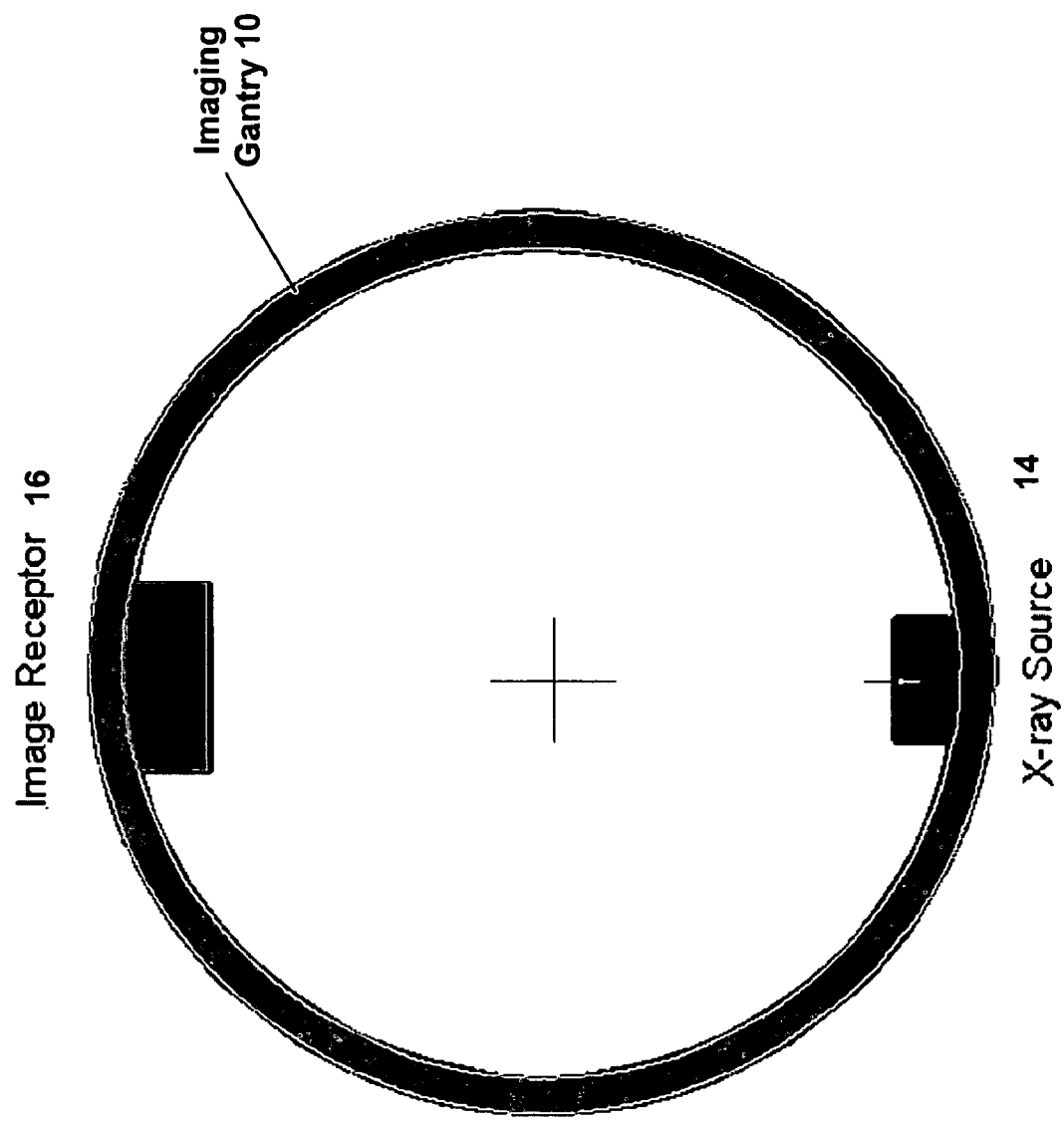
FIG. 2 illustrates a circular gantry/O-arm with an image receptor and image source according to an embodiment of the invention.

In an embodiment of the invention, the plurality of two-dimensional image exposures may be utilized to provide partial images or to emulate other medical imaging equipment. A group of the two dimensional images may be utilized to provide partial images on a three-dimensional map. Under other operating conditions, the group of two-dimensional images may be displayed to the user on the display device, without being placed on a three-dimensional device. In other words, the display device can be configured to display one image or a plurality of two-dimensional images. This feature allows the three dimensional imaging system to emulate medical imaging systems that provide one or multiple two-dimensional images. Under other operating conditions, the three-dimensional imaging system may be configured to only provide a partial three-dimensional image from a subset of the plurality of two-dimensional images. For example, the three-dimensional imaging system may create a three-dimensional image of only the left upper chest, left arm and left torso. In an embodiment of the invention, the plurality of two-dimensional images can be utilized to generate a single or multiple two-dimensional image(s) from any or all locations acquired by the device. The at least one subject sensor 12, the at least one image source 14, and the at least one image receptor 16 may be located within an inner circumference of the imaging gantry 10. The imaging gantry 10 may be referred to as an O-arm. The imaging gantry 10 may be tubular in shape. The imaging gantry 10 may be rectangular, square, or trapezoidal in shape. In embodiments of the invention, the imaging gantry 10 may be five-sided, six-sided, seven-sided, eight-sided, or more. FIG. 2 illustrates a tubular imaging gantry 10 (O-arm) with an image receptor 16 and image source 14 according to an embodiment of the invention. In an embodiment of the invention, the inner circumference may rotate about the subject while the imaging gantry 10 is in a fixed position. In an embodiment of the invention, the entire imaging gantry 10 may rotate about the subject. The subject's location is illustrated as a "+" in FIG. 1 and the subject may be placed in a position in or near the center of the interior portion of the imaging gantry 10, i.e., in the center of the tube illustrated in FIG. 1. The at least one image source 14 and the at least one image receptor may rotate about the inner circumference of the imaging gantry 10 in order to provide a plurality of two-dimensional image exposures of the subject.

Figure 3:
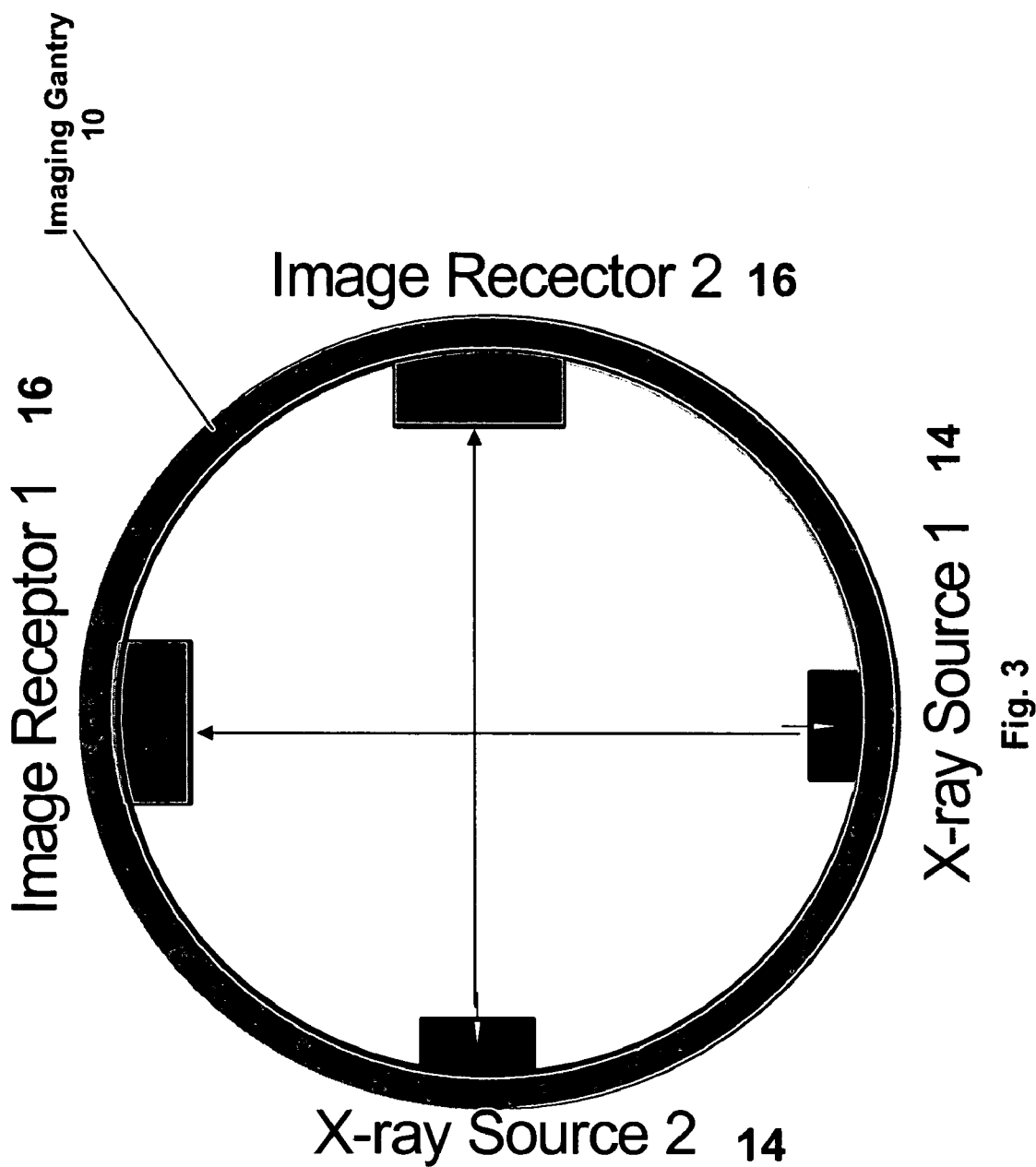
FIG. 3 illustrates an image receptor and an image source according to an embodiment of the invention.

In another embodiment of the present invention, more than one image source 14 and more than one image receptor 16 may be utilized by the imaging gantry 10. If more than one image source 14 and more than one image receptor 16 are utilized, the number of image sources 14 may be equal to the number of image receptors 16, and the image source 14 and the image receptor 16 may be located directly across from each other within the inner circumference of the imaging gantry 10, as illustrated by FIG. 3. This may enable the image receptors 16 to receive the full intensity of the image sources' 14 beam. In alternative embodiments of the present invention, the number of image sources 14 may be less than the number of image receptors 16 where multiple image receptors 16 may receive a single image source's 14 beam.

Figure 4:
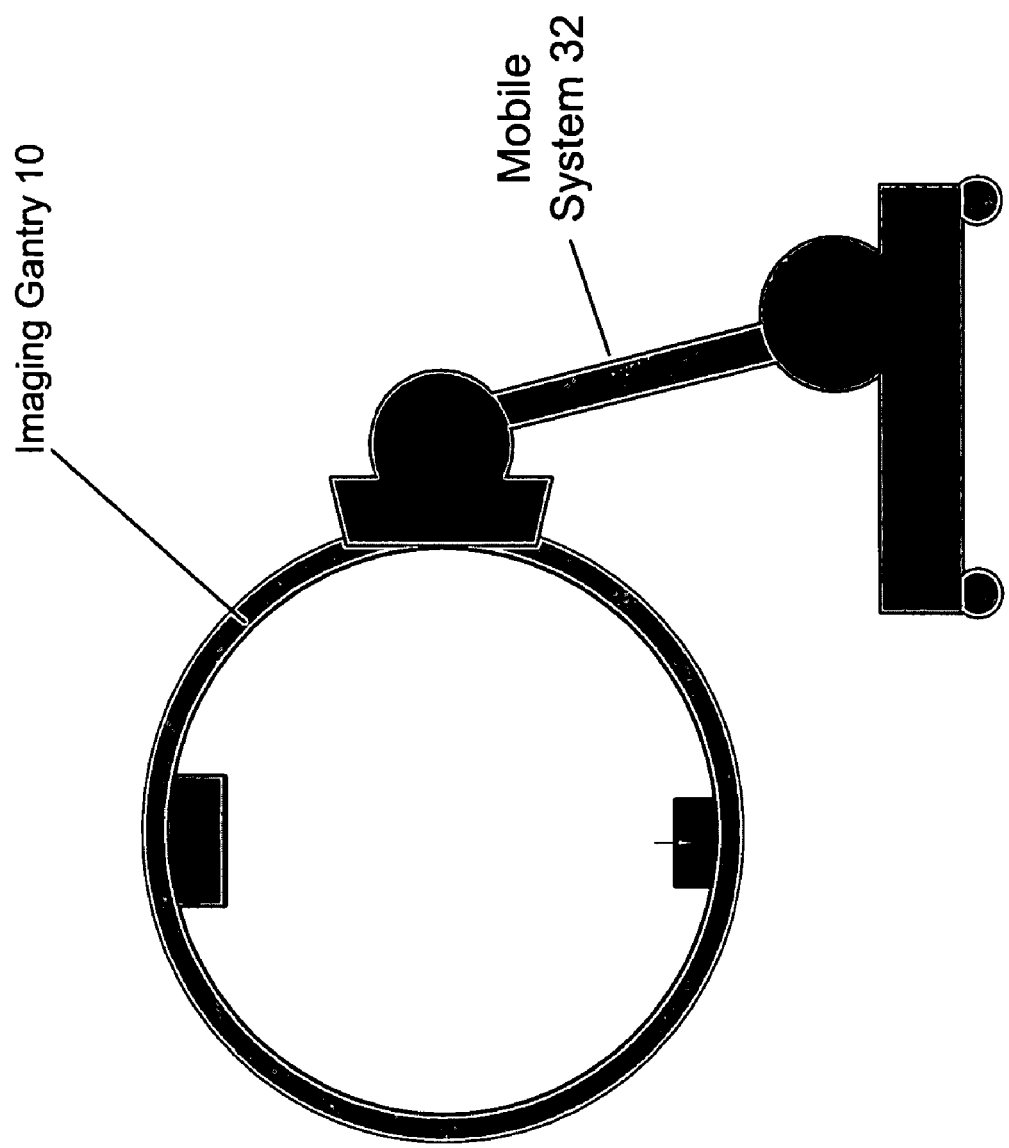
FIG. 4 illustrates a mobile three-dimensional imaging system according to an embodiment of the present invention.

The three-dimensional imaging system may be a fixed system or a mobile system. The fixed system may include a table 30, on which the subject lays during examination, wherein the table 30 is linked to an apparatus within the three-dimensional imaging system, such as the computing device 24. The table 30 may be linked to the computing device 24 to allow for movement in either a vertical or horizontal direction. Alternatively, the table 30 may be linked to a controller or a controller may be included within the table 30. The computing device 24 may interface with the controller to identify whether the table 30 should be moved up or down in a vertical or a horizontal direction. Alternatively, the three-dimensional imaging system may be a mobile system, as illustrated in FIG. 4. The imaging gantry 10 may be connected to a mobile system 32 which is moved to the desired angle relative to the subject, when the subject lies on the same position on the table 30.

The three-dimensional imaging system may also emulate a CT scanner hardware and software. The three-dimensional imaging system may utilize a 360 degree gantry with opposing x-ray source(s) and imaging receptor(s). Modifications to this approach may allow imaging similar to CT imaging. The three-dimensional imaging system could add a fulcrom reference. The addition is performed either by installing actual hardware and software to add the fulcrom, or by emulating the fulcrom utilizing software alone. The three-dimensional imaging system could acquire the images utilizing the fulcrom reference (via tomography) and have these images computerized and displayed, as described above in the discussion of the operation of the three-dimensional imaging system. The MR technology is similar to CT and the same approach could be utilized with MR technology.

The three-dimensional imaging system may also be utilized to emulate ultrasound devices. Ultrasound software is similar to a CT or an MR in the sense that an ultrasound system provides images based on interpolation of depth information, where the depth information is gathered via the use of sound waves. The three-dimensional imaging system sensors, which in this case could be ultrasound depth sensors requiring physical contact with the subject to be imaged, may gather depth readings regarding the object to be imaged. The three-dimensional imaging system may utilize the depth readings in combination with pre-established algorithms, geometry calculations, and/or the inverse square law to provide an image that emulates ultrasound. In an embodiment of the invention, the three-dimensional imaging system sensors could be ultrasound sensors which provide depth information without requiring physical contact with the subject to be imaged.

The three-dimensional imaging system may have the ability to utilize single and multiple imaging collimation schemes. For example, the three-dimensional imaging system may utilize focused beam, cone beam, or fan beam schemes, or may use a combination of the three imaging and collimation schemes. Additional collimation schemes may also be utilized. These collimation schemes are commonly used in medical imaging and can easily be added mechanically with 1) hardware or 2) software only.

The three-dimensional imaging system may be utilized in the following medical imaging applications: 1) computerized tomography; 2) mammography; 3) digital radiography; 4) radiography; 5) fluoroscopy; 6) fluorography; 7) fluoroscopy CT; 8) radiography/fluoroscopy; 9) bone densitometry; 10) dental radiography; 11) dental panoramic imaging—fluoroscopic and radiographic; 12) three-dimensional dental imaging (partial, 360 degrees, panoramic, radiographic—either in real time or reconstructive); 13) cancer therapy; 14) brachytherapy; and 15) simulation of x-rays.

The three-dimensional imaging system may be utilized in other non-medical imaging applications such as non-destructive testing, homeland security; and computer entertainment. The homeland security applications may include baggage screening or person screening. The computer entertainment applications may include computer gaming, broadcast media; films; internet, virtual reality, and other computerized applications.

Illustratively, in the non-destructive testing application, a device (such as circuit board, a system, an airplane fuselage, or a component) may be subjected to quality assurance testing, e.g., may be operated under real-life or high stress conditions for a certain period of time. After the testing is complete the circuit board, system, airplane fuselage, or component may be analyzed by the three-dimensional imaging system to determine if the device still has the necessary structural integrity, e.g., no cracks in the structure or no warping. The device may be placed on a conveyor belt and moved to a position within an imaging gantry. As discussed above, a computing device within the three-dimensional imaging system may determine a device volume and device location in order to create a base three-dimensional map. Alternatively, some of the device volume and device location information may be pre-programmed into the computing device, and this information may be utilized to create the base three-dimensional map for the device. The computing device may then receive a plurality of digital two-dimensional image exposures and create a three-dimensional image exposure by overlaying, pasting, or interpolating the plurality of two-dimensional image exposes on the base three-dimensional map of the device.

In homeland security applications, the three-dimensional imaging system may operate in the same fashion as described above for the non-destructive testing. In the baggage screening applications, a conveyor belt may be utilized to transport the luggage past the imaging gantry. In the person screening application, the person may walk into an area scanned by the imaging gantry. In certain homeland security applications, the imaging gantry may be imaging the person to gather biometric information, for example, fingerprints, retina scans, facial features; facial patterns, mole location.

In the computer entertainment applications, the person may be present in an area scanned by the imaging gantry. As discussed above, a three-dimensional image exposure may be created of the person. In an embodiment of the invention, a plurality of three-dimensional image exposures may be created of the person and the plurality of three-dimensional image exposure may be of the person in different positions or poses. The three-dimensional image exposure(s) may be stored on a computing device and may be utilized as real-life replicas of the persons in video games, virtual reality games, or on websites visited by the user (or person). In other words, the three-dimensional image exposures may be transmitted to systems which include the software for the video games, virtual reality games, etc. In films or other entertainment mediums, a plurality of images, with the person in multiple poses, may be utilized to present the person in motion in the film or in a variety of poses which may be interpolated into motion. In these applications, because the three-dimensional image exposure(s) are created from the person directly, the three-dimensional image exposure(s) are more detailed and realistic.

Figure 5:
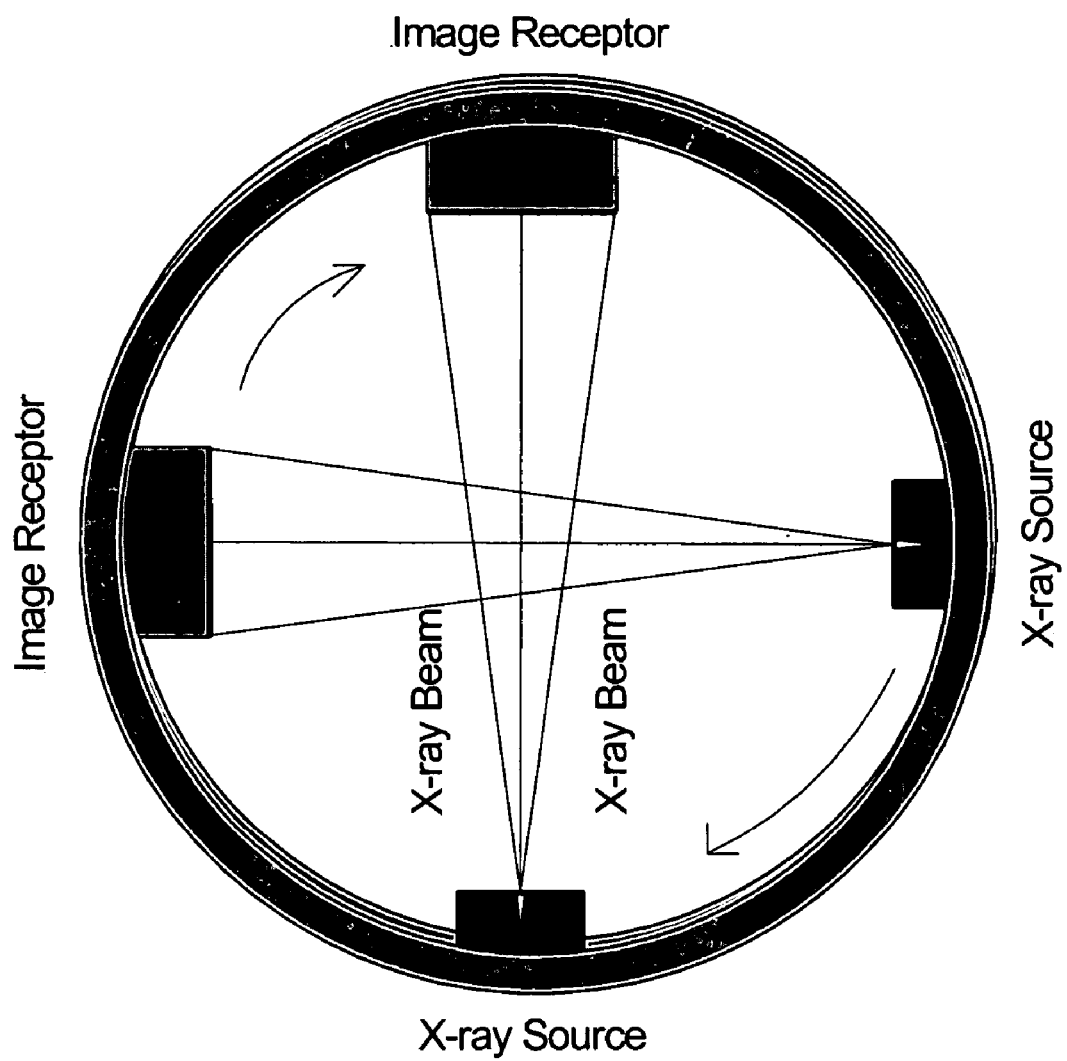
FIG. 5 illustrates the user of two subject sensors in an imaging gantry according to an embodiment of the present invention.
Figure 5B:
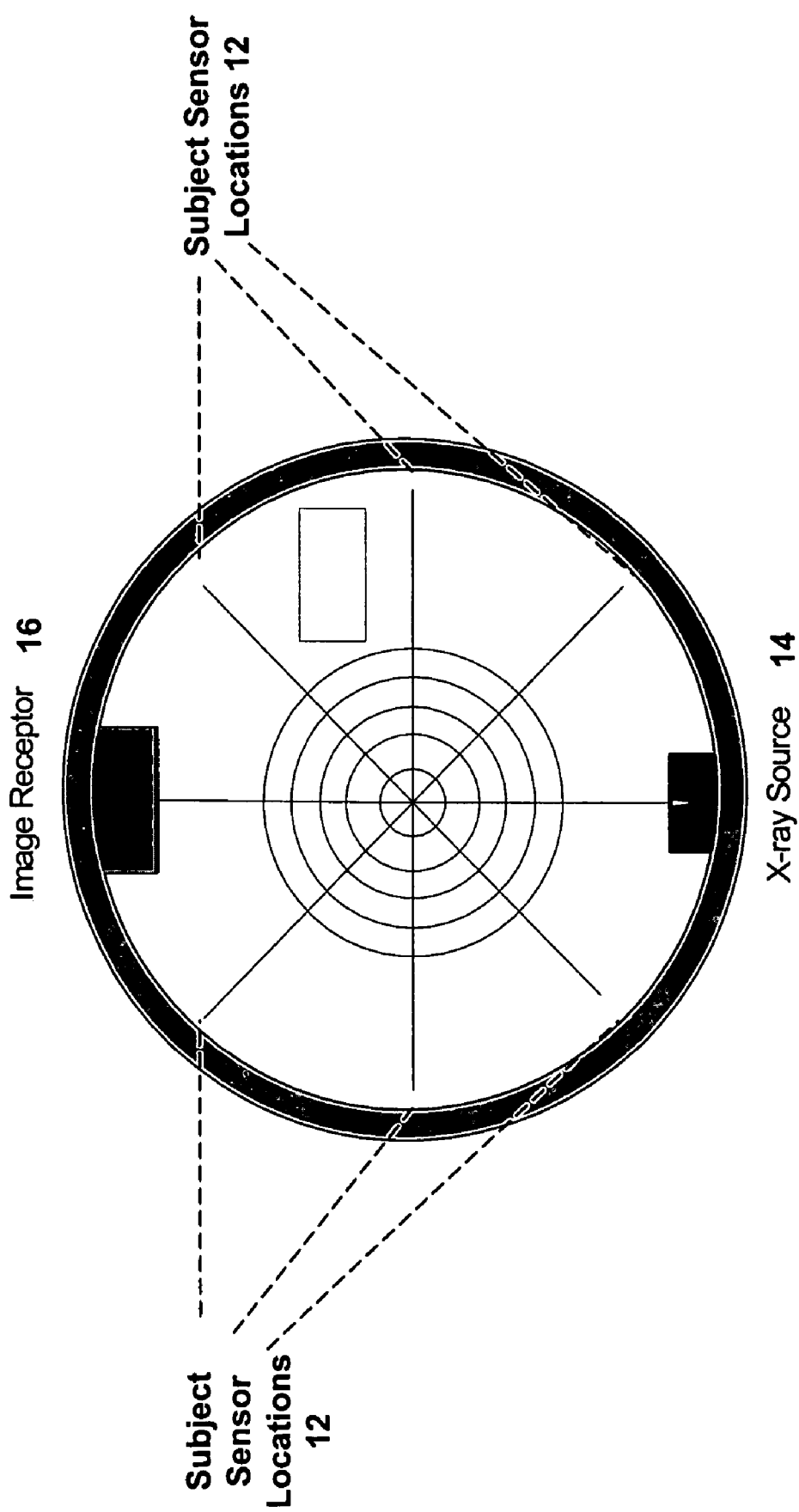
FIG. 5b illustrates a depth of the subject sensor mapping according to an embodiment of the invention.

The subject sensor 12 may provide distance readings and reference readings which correspond to the distance and angle between the subject sensor 12 and the subject. The at least one image source 14 and the at least one image receptor 16 may be located perpendicular to a subject. The subject sensor 12 may provide the distance reading from the image source 14 and the image receptor 16 pair to the subject. In embodiments of the invention, more than one subject sensor 12 may be utilized. FIG. 5a illustrates how a plurality of subject sensors 12 may map patient depth within the imaging gantry 10 according to an embodiment of the invention. FIG. 5b illustrates the depth of the subject sensor mapping according to an embodiment of the invention. The subject sensor 12 may be located on the inner circumference of the imaging gantry 10. The at least one subject sensor 12 may rotate around the inner circumference of the imaging gantry 10, which means the at least one subject sensor 12 may rotate around the subject, and provide a plurality of distance readings and a plurality of reference readings. Alternatively, a plurality of subject sensors 12 may be stationary and provide a plurality of distance readings and a plurality of reference readings.

In an embodiment utilizing a plurality of subject sensors 12, the plurality of subject sensors 12 may be equally spaced within the inner circumference of the circular gantry 10. The subject sensor 12 or the plurality of subject sensors 12 may provide the distance from the inner circumference of the imaging gantry 10 (and therefore the distance from the at least one image source 14 and the at least one image receptor 16), i.e., distance readings, to the subject. If a large number of subject sensors 12 are utilized, the plurality of subject sensors 12 may not be rotated as far about the subject in order to determine the location of the subject. If only one subject sensor 12 is utilized or a small number of subject sensors 12 are utilized, the subject sensors 12 may need to be rotated almost 360 degrees about the subject to generate enough distance measurements to produce a three-dimensional map of the subject.

Figure 6:
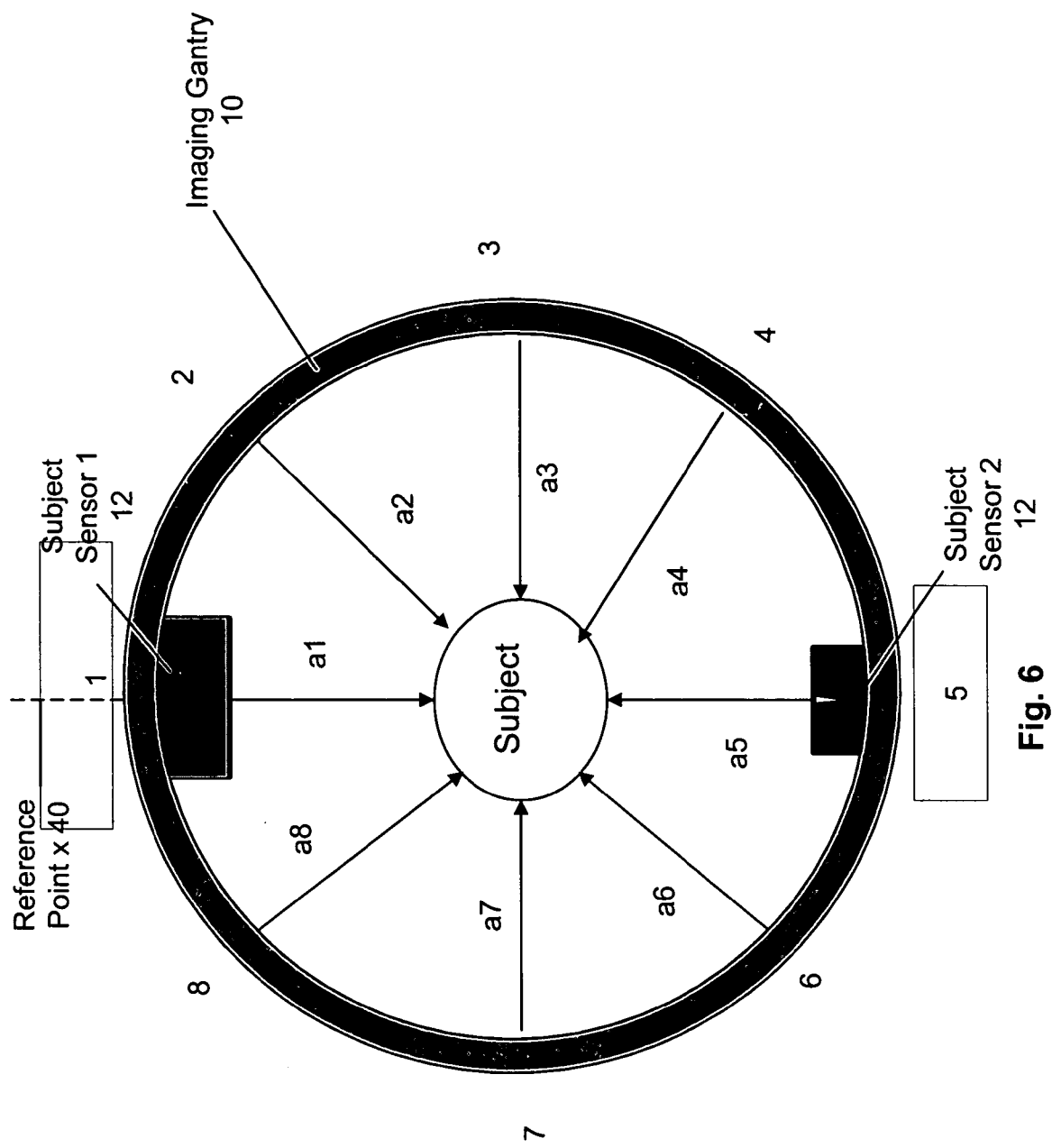
FIG. 6 illustrates two subject sensors providing a plurality of distance readings and a plurality of reference readings according to an embodiment of the invention.

If the subject sensor 12 is rotated, the subject sensor 12 may also provide a plurality of reference readings regarding its location relative to an imaging gantry reference location in order to identify the angle at which the subject sensor 12 is gathering its distance reading. For example, two subject sensors 12 are illustrated in an imaging gantry in FIG. 5. Initially, the two subject sensors 12 (subject sensor 1 and subject sensor 2) provide a distance from the subject sensors 12 to the subjects, i.e., in FIG. 6, the distance a1 is measured from subject sensor 1 to the subject and the distance a2 is measured from subject sensor 2 to the subject. The angle away from the imaging gantry reference point x 40, i.e., the reference reading is 0 for distance a1 and 180 degrees for distance a5 because location a1 is measured from the imaging gantry reference point x 40. In order to provide enough information to generate a 360 degree three-dimensional map of the subject, the subject sensors 12 may need to be rotated to a plurality of positions. In FIG. 6, subject sensor 1 12 and subject sensor 2 12 may be rotated 45 degrees to positions 2 and 6, respectively, and may provide distance readings to the subjects of a2 and a6, respectively, along with reference readings of 45 degrees clockwise for a2 and 235 degrees clockwise for a6. The subject sensor 1 12 and subject sensor 2 12 are rotated twice more, in increments of 45 degrees, to provide distance readings of a3, a4, a7, and a8, as illustrated in FIG. 6, and reference readings of 90, 135, 270 and 350 degrees respectively. Thus, in this illustration, eight distance readings and eight reference readings may be generated in order to provide information to generate a base three-dimensional map. In order to get a better representation of the subject, more distance readings and reference readings may have to be gathered. This may be accomplished by either adding more subject sensors 12 or by rotating the subject sensors 12 a smaller number of degrees each time a measurement is taken.

The subject sensor 12 may be an external environmental sensor, as is well known in the art. The subject sensors 12 may be rangefinders, infrared devices, sound-echoing sensors, or other similar technologies that are able to detect the presence of a subject and the distance from the sensor to the subject. For example, the Sharp™ GP2DO2 Infrared Distance Sensor provides distance readings from the sensor to the subject by transmitting or emitting an infrared light off the subject and utilizing an array of photodetectors to measure the reflected infrared light off the subject. The distance readings between the subject and the subject sensor 12 are determined by the portion of the array of photodetectors which receives the reflected infrared light based on the parallax of the outgoing and incoming rays of the infrared light.

In an embodiment of the present invention, the subject sensor 12 or the plurality of subject sensors 12 may gather the distance reading and the reference reading at each rotation and may transmit each distance reading and reference reading to the computing device 24. In an alternative embodiment, the subject sensors 12 or the imaging gantry 10 may include memory (not shown) to store the distance readings and the reference readings and may transmit the distance readings and the reference readings for the subject only when the rotation about the subject has completed. Alternatively, the subject sensors 12 may transmit the distance readings and the reference readings to the computing device 24 at specific time intervals.

A location determination module, within the computing device 24, may receive the plurality of distance readings and the plurality of reference readings and interpolate the plurality of distance readings and the plurality of reference readings to determine a subject location and a subject volume. The location determination module may utilize pre-calibrated physics calculations and the inverse square law to determine the subject location and the subject volume. For example, the subject sensor 12 or the plurality of subject sensors 12 may send the distance readings to identify the distance of the subject from the subject sensor 12 and the reference readings to identify from what view or angle the distance is calculated from. The location determination module may utilize the inverse square law to determine the depth of the subject and the magnification of what is being imaged.

The subject location and the subject volume may be transmitted from the location determination module to a map module, also located within the computing device 24. The map module may receive the subject location and subject volume information and create a base three-dimensional map of the subject. The base three-dimensional map may be utilized as the underlying representation of a base three-dimensional image exposure. The base three-dimensional image exposure may serve as the model on which the continuous updates or the real-time updates of the three-dimensional image exposures may be overlaid, pasted, or interpolated to create an updated three-dimensional image exposure.

The at least one image source 14 and the at least one image receptor 16 may be located within the inner circumference of an imaging gantry 10. The number of image sources 14 and image receptors 16 installed within an inner circumference of the imaging gantry 10 may be equivalent, meaning if there is one image source 14, there is one image receptor 16 and if there are three image sources 14, then there are three image receptors 16. Alternatively, the number of image receptors 16 may be larger than the number of image sources 14 with multiple image receptors 16 receiving information from the smaller number of image sources 14. Also, multiple image sources 14 could be utilized in conjunction with one or a plurality of image receptor(s) 16. In this embodiment, the number of image source(s) 14 may be equal to or greater than the number of image receptor(s) 16. In one embodiment, the at least one image source 14 and the at least one image receptor 16 may be positioned 180 degrees apart from each other as illustrated in FIGS. 2 and 3.

The at least one image receptor 16 and the at least one image source 14 may move synchronously with each other or parallel to each other in a clockwise or counterclockwise motion. The at least one image receptor 16 and the at least one image source 14 may move asynchronously from each other. In this embodiment, illustratively, the image receptor and image may start out parallel from each other. In an embodiment of the invention, the at least one image source 14 and the at least one image receptor 16 may be offset in configuration or alignment. Thus, an image source 14 and an image receptor 16 may be referred to as an imaging set. The imaging set may be rotated in a direction perpendicular to the subject.

Figure 7:
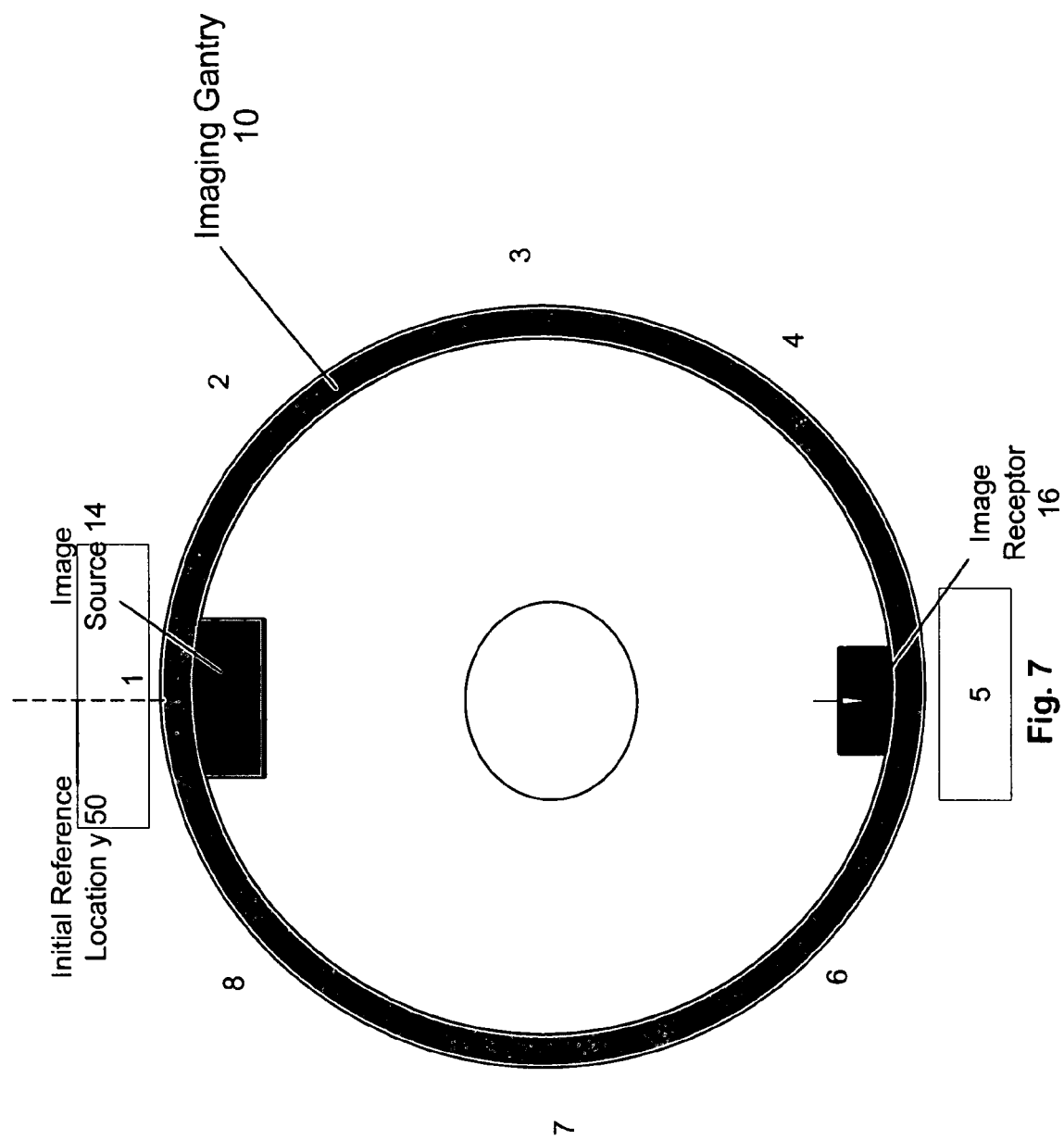
FIG. 7 illustrates the image receptor collecting a plurality of two-dimensional image exposures produced when the image source passes around the subject.

The imaging set may be rotated about the inner circumference of the imaging gantry 10 by a stepping motor located within the imaging gantry 10. Alternatively, the imaging set may be rotated by a motor which receives instructions from an encoder. Illustratively, the stepping motor may receive instructions to move to a specific location on the inner circumference of the imaging gantry 10. For example, as illustrated in FIG. 7, the stepping motor may receive instructions to move the image source 14 of the imaging set to a specific location 2 of the imaging gantry, which in turn would move the image receptor 16 of the imaging set to a specific location 6 of the imaging gantry 10. Once the image source 14 and the image receptor 16 reach specific locations 2 and 5 respectively, the image source 14, the image receptor 16, or the stepping motor, encoder, or imaging set moving device may provide associated reference information about the locations, i.e. associated reference locations, e.g., the image source 14 is shifted 45 degrees clockwise from an initial reference point and the image source 14 may transmit a beam from this location to the image receptor 16. The image source 14 may be shifted or rotated in whole or in part, either clockwise or counter clockwise. In addition, 45 degrees is merely illustrative and the image source may be rotated utilizing a degree measurement from 0 to 360 degrees.

In an embodiment of the invention utilizing one image source 14 and one image receptor 16, the imaging set may be rotated to obtain complete coverage of the subject, which may include some overlapping of the coverage area. For example, if the inner circumference of the tubular imaging gantry 10 is 120 inches, i.e., ten feet, and a single image receptor 16 has a reception width of twelve inches, the imaging set may need to be moved or stepped approximately eleven times around the inner circumference of the imaging gantry 10 to complete a 360 degree scan. In alternative embodiments, a plurality of imaging sets may allow a fewer number of rotations or steps, e.g., two imaging sets may only need six movements to complete a 360 degree scan.

Each time the imaging set is moved, either the image source 14, the image receptor 16, or the stepping motor may provide a reference location of the imaging set in regards to an initial reference location y 50, illustrated in FIG. 7. The reference location of the imaging set in regards to the initial reference location y 50 may be established in order to correlate the information received by the imaging receptor 16 and place the two-dimension image exposures onto the correct portion of the base three-dimensional map. Illustratively, if the imaging information is collected from by the image receptor 16 when the image source 14 is transmitting a beam through the right side of the subject, the information may be tagged with a reference location to indicate that this image receptor 16 reading, after conversion to a digital two-dimensional image exposure, may be placed onto the portion of the base three-dimensional map corresponding to the right hand side of the subject. The reference location should be correlated with the reference reading from of the at least one subject sensor 12 in order to match up the digital two-dimensional image exposure with the correct area of the base three-dimensional map created by the map module. For example, as illustrated in FIGS. 6 and 7, if the subject sensor 12 provides a distance from the subject to the subject sensor as a2 when the subject sensor 12 is in position 2, and the location determination module calculates a subject position and depth from the position 2 based on the distance reading a2, then the digital two-dimensional image exposures created when the image source 16 of the imaging set is at position 2 should be correlated to the section of the base three-dimensional map created by the distance reading from the subject sensor 12 when the subject sensor 12 is at position 2.

In an embodiment utilizing one image source 14 and one image receptor 16, the image receptor 16 may collect a two-dimensional image exposure produced when the beam from the image source 14 passes through the subject, as illustrated in FIG. 7, for each location within the inner circumference of the imaging gantry 10 the imaging set is rotated to. Included with the two-dimensional image exposure may be the associated reference location, i.e., where the imaging set was located on the inner circumference of the imaging gantry 10 when the image receptor 16 collected the two-dimensional image exposure. A plurality of two-dimensional image exposures, along with the associated reference information, may be produced for a number of different locations when the imaging set is rotated about the inner circumference of the imaging gantry 10.

An image receptor 16 may include an image receptor device, an image intensifier, and a camera mounted on the image intensifier's output phosphor to collect video image data. Alternatively, the image receptor 16 may include an image receptor device and a charge coupled device (CCD) image intensifier device, wherein the CCD image intensifier device itself collects video image data. In another alternative embodiment, the image receptor 16 may include an image receptor device itself that converts the received image exposure information into either digital or analog information, rather than into video information. The image receptor 16 may produce the plurality of two-dimensional image exposures in a digital, analog, video, or other similar format. Also, the image receptor 16 may receive the plurality of reference locations from the image source 14 or the imaging gantry 10, and include the plurality of associated reference locations for each of the plurality of two-dimensional image exposures.

In an embodiment of the invention utilizing one image source 14 and one image receptor 16, the plurality of two-dimensional image exposures and the plurality of associated reference locations collected by the image receptor 16 may be immediately transmitted to a computing device 24. Alternatively, the image receptor 16 or the imaging gantry 10 may include a buffer memory (not shown) in order to collect all of the plurality of two-dimensional image exposures for a subject, e.g., if there are twelve steps or semi-rotations then twelve scans may be collected. The image creation module, within the computing device 24, may receive the plurality of two-dimensional image exposures and the plurality of associated reference locations The three-dimensional imaging system may also include a computing device 24. In addition, the three-dimensional imaging system may include a controller for controlling the physical movements of the imaging gantry 10 and/or the physical movements of the table 30 on which the subject may be placed. Methods of controlling the physical movements of the imaging gantry 10 and/or the table 30 are well known in the art, e.g., CT technology utilizes controllers or similar devices to control physical movements of the imaging gantry 10 or the table 30 on which the subject is placed.

The computing device 24 may include an image digitizer 20 implemented in hardware or software. Illustratively, the image digitizer 20 may be a printed circuit board installed in a Peripheral Control Interface slot in the computing device 24. Alternatively, the image digitizer 20 may be a separate physical device from the computing device 24. Image digitizers 20 are well known in the art, e.g., Matrox Cronos™ frame grabber products.

In one embodiment of the present invention, the image creation module, in the computing device 24, may receive the plurality of two-dimensional image exposures along with the plurality of associated reference locations directly from the image receptor 16 utilizing wireless or line communication technologies or protocols. The image creation module may utilize the image digitizer 20 to receive and to digitize the plurality of two-dimensional image exposures to create a plurality of digital two-dimensional image exposures. Illustratively, the image digitizer 20 may digitize the received two-dimensional image exposures at a rate of between 30 to 60 frames a second if the input is a video signal. In other embodiments where only one or two frames are input to the digitizer 20 from the image receptor 16, only one or two frames may be digitized.

Figure 8A:
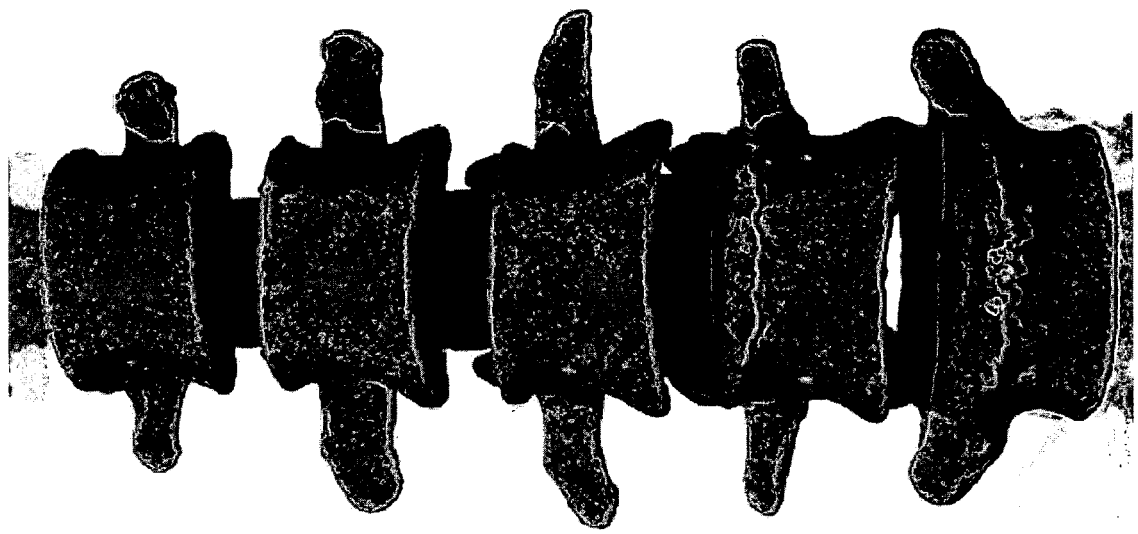
FIG. 8a illustrates a three-dimensional image exposures of a spine as presented in an anterior-posterior view, i.e., from front-to-back, according to an embodiment of the invention.

The map module, within the computing device 24, may include the base three dimensional map. The map module may transfer the base three-dimensional map to an image creation module. The image creation module may receive the plurality of digitized two-dimensional image exposures along with the plurality of associated reference information from the imaging module. The image creation module may paste or overlay the plurality of digital two-dimensional image exposures onto the base three dimensional map utilizing the plurality of associated reference information to identify which section of the base three-dimensional map is to receive which of the plurality of digital two-dimensional image exposures. The pasting or overlaying of the plurality of digital two-dimensional image exposures may create a base three-dimensional fluoroscopic image. The image creation module may continue to paste or overlay the plurality of digital two-dimensional image exposures onto the base three-dimensional map until the base three-dimensional image exposures represents a 360 degree view of the subject. Alternatively, the plurality of digital two-dimensional image exposures may be interpolated onto the base three dimensional map using a math formulation or algorithm, which creates a base three-dimensional image exposure. The base three-dimensional image exposure may be transferred from the computing device 24 to the display device 28 utilizing RS-422 serial, serial, fiber optic, parallel, or any data and image transfer communication protocol. The medical personnel may view the base three-dimensional image exposure on the display device 28 immediately or within a few seconds after the first scan was initiated A viewing angle on the display device 28 may be selected for the base three-dimensional image exposure or a default value for the viewing angle of the base three-dimensional image exposure may be input into the image creation module. Illustratively, a viewing angle may be anterior-to-posterior, right side-to-left side, 15 degrees clockwise from anterior-to-posterior view, etc. FIG. 8a illustrates a base three-dimensional image exposure generated according to an embodiment of the present invention. In FIG. 8a, the base three-dimensional image exposure of the spine is presented in an anterior-posterior view, i.e., from front-to-back, according to an embodiment of the invention. In one embodiment of the present invention, the base three-dimensional image exposure may not be displayed until the base three-dimensional image exposure has been constructed. Alternatively, sections of the base three-dimensional image exposure may be displayed as the pasting, interpolating, or overlaying process is occurring.

Figure 8B:
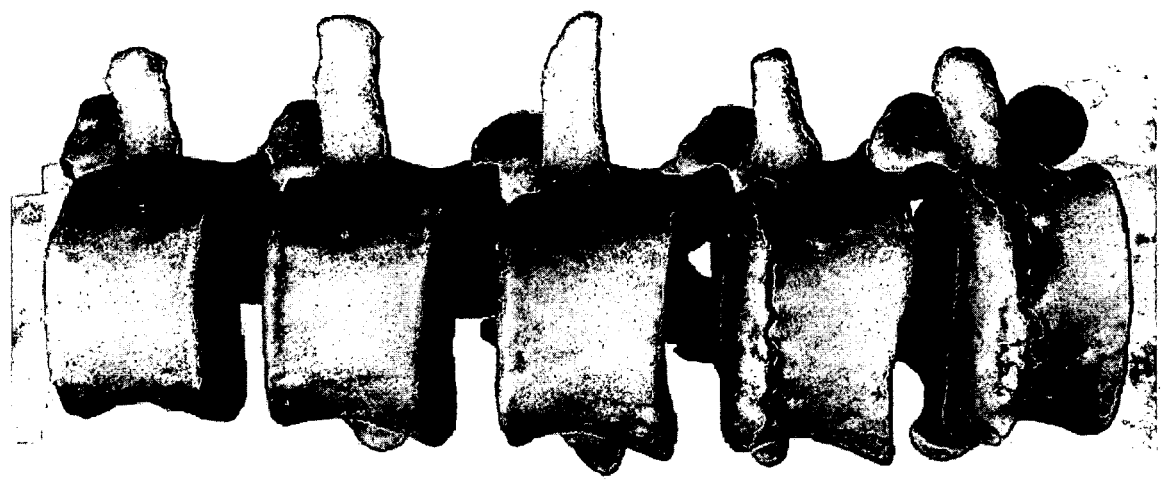
FIG. 8b illustrates a three-dimensional image exposures of a spine rotated counterclockwise in a caudal manner according to an embodiment of the invention.

A system operator may select to change the viewing angle on the display device 28 for the base three-dimensional image exposure. The system operator may change the viewing angle by notifying the image creation module by any method well known in the art. FIG. 8b illustrates FIG. 8a rotated slight caudal (towards the hind side of the subject) from center, in this case to allow a better view of the spinal canal and the side of a vertebrae. The viewing angle of the base three-dimensional image exposure may be rotated up to 360 degrees from the original selected viewing angle, all depending upon the viewing angle the operator desires in order to view the procedure from the most optimal angle. The rotation of the base three-dimensional image exposure may occur by any method well-known in the art for rotating three-dimensional images on the display device 28, utilizing the computing device 24 and its memory if necessary. A change in the viewing angle may not require any additional scans or utilization of the imaging set, i.e., image source 14 or image receptor 16, or the imaging gantry 10 in any manner.

The operator may also select an image section on the display device 28 for viewing a specific portion of the base three-dimensional image exposure, e.g., for viewing the angioplasty device moving through the vein or artery. The image selection module may allow the operator to select more than one image sections. The image section may correspond to the area where the procedure is taking place. The image selection module may divide up the base three-dimensional image exposures into different image sections which may be indicated on a display of the computing device. In one embodiment of the present invention, the user may select one or a plurality of the image sections for updating. In one embodiment, the user may select all of the image sections for updating. Unlike prior art systems, the updating of the selected imaging sections, even if all of the imaging sections are selected, may occur in real-time or continuously.

Figure 9:
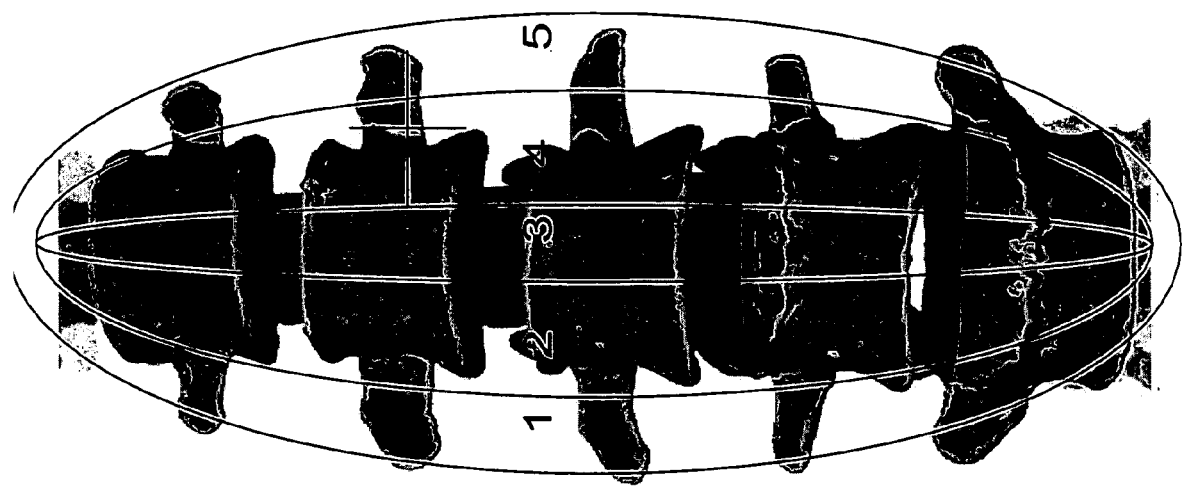
FIG. 9 illustrates a three-dimensional image exposure of a spine divided into a plurality of imaging sections according to an embodiment of the invention.

Illustratively, the entire viewing area on the display device 28 may be 360 degrees, i.e., a complete circle, and the plurality of imaging sections may be divided up so that the addition of all of the imaging sections may equal the entire 360 degree viewing area. For example, if six imaging sections are generated, then each of the six imaging sections may represent a 60 degree angle of the subject. As illustrated in FIG. 9, the operator may select a plurality of image sections, e.g., in this illustration image sections 4 and 5 are selected. In an embodiment of the invention, if the viewing angle does not correspond to the selected image sections, the three-dimensional image exposure may be rotated to a viewing angle corresponding to the selected image sections, as described previously.

Once the imaging section or the plurality of imaging sections are selected, the alignment module may align the imaging set, i.e., image source 14 and image receptor 16, to provide the at least one two-dimensional image exposure of the selected image sections. Thus, the imaging set may be moved via commands from the alignment module, which may be located within the computing device 24, indicating a start position that the imaging set should be placed in order to provide the at least one two-dimensional image exposure for the imaging section or sections selected. In one embodiment, the alignment module may receive the reference locations for each of the digital two-dimensional image exposures which were utilized to create the base three-dimensional image exposures. When the operator selects the image section or image sections to be updated, the alignment module may identify the associated reference location or reference locations corresponding to the selected image section(s), and output this information. For example, utilizing FIG. 9, the operator may select imaging sections 4 and 5. This corresponds to, assuming a reference point of looking outward from the subject, the left front view of the subject and the left side view of the subject. In order to provide the at least one two-dimensional image exposure of the selected imaging sections, the imaging set may need to be ganged or moved to locations 2 and 3 of FIG. 5, which are the locations where the image source 14 transmits rays through the left front view of the subject. Because multiple imaging sections may be selected, the alignment module may provide instructions to move or step the imaging set to the appropriate reference location or reference locations to provide the required imaging. Illustratively, the alignment module may provide the reference locations for the selected image sections to the imaging set in the imaging gantry 10. In the example illustrated in FIG. 5, the reference locations corresponding to the selected imaging sections are locations 2 and 3. The imaging set may only move in the area to provide the at least one updated two-dimensional image exposures for the selected image sections, which in some embodiments may be all the image sections. The image set, i.e., image source 14 and image receptor 16, may move to all the reference locations necessary to capture images for the selected image sections.

Once the imaging set is moved to capture the at least one two dimensional image exposure of the selected imaging sections, the image module, within the computing device 24, may start to receive the at least one updated two-dimensional image exposure for the selected image sections from the imaging set along with the at least one associated updated reference location for the at least one updated two-dimensional image exposures. Because the selected image sections may generally be smaller than a 360 view of the subject, the at least one updated two-dimensional image exposure may be provided to the image module of the computing device 24 at a faster rate. In one embodiment of the present invention, the image module may receive the at least one updated two-dimensional image exposure and may digitize, at the digitizer 20, the at least one updated two-dimensional image exposure to create at least one digital updated two-dimensional image exposure. The at least one updated digital two-dimensional image exposures may be transferred to an update module. The update module may receive the at least one updated digital two-dimensional image exposure along with the at least one associated updated reference and overlay, interpolate, or paste the at least one updated digital two-dimensional image exposure on the base three-dimensional image exposure to create an updated three-dimensional image exposure. In this embodiment of the invention, only the selected imaging sections of the base three-dimensional image exposure area may be updated by the received plurality of digital two-dimensional image exposures. Illustratively, utilizing FIG. 9, only image sections 4 and 5 may receive updated imaging information, i.e., the at least one updated digital two-dimensional image exposure, while the other imaging sections of the base three-dimensional image exposure may utilize the original plurality of digital two-dimensional image exposures and not receive any updated digital two-dimensional image exposures. In one embodiment, all of the at least one updated digital two-dimensional image exposures may be collected for all the selected imaging sections before the updated three-dimensional image exposure may be displayed on the display device 28. In an alternative embodiment, each digital updated two-dimensional image exposure which updates the base three-dimensional image exposure may be displayed immediately on the display device 28 once the image update module overlays, pastes, or interpolates it on the base three-dimensional image exposure. After the at least one digital updated two-dimensional image exposure is overlaid, interpolated, or pasted onto the base three-dimensional image exposure, an updated three-dimensional image exposure is created.

Figure 10:
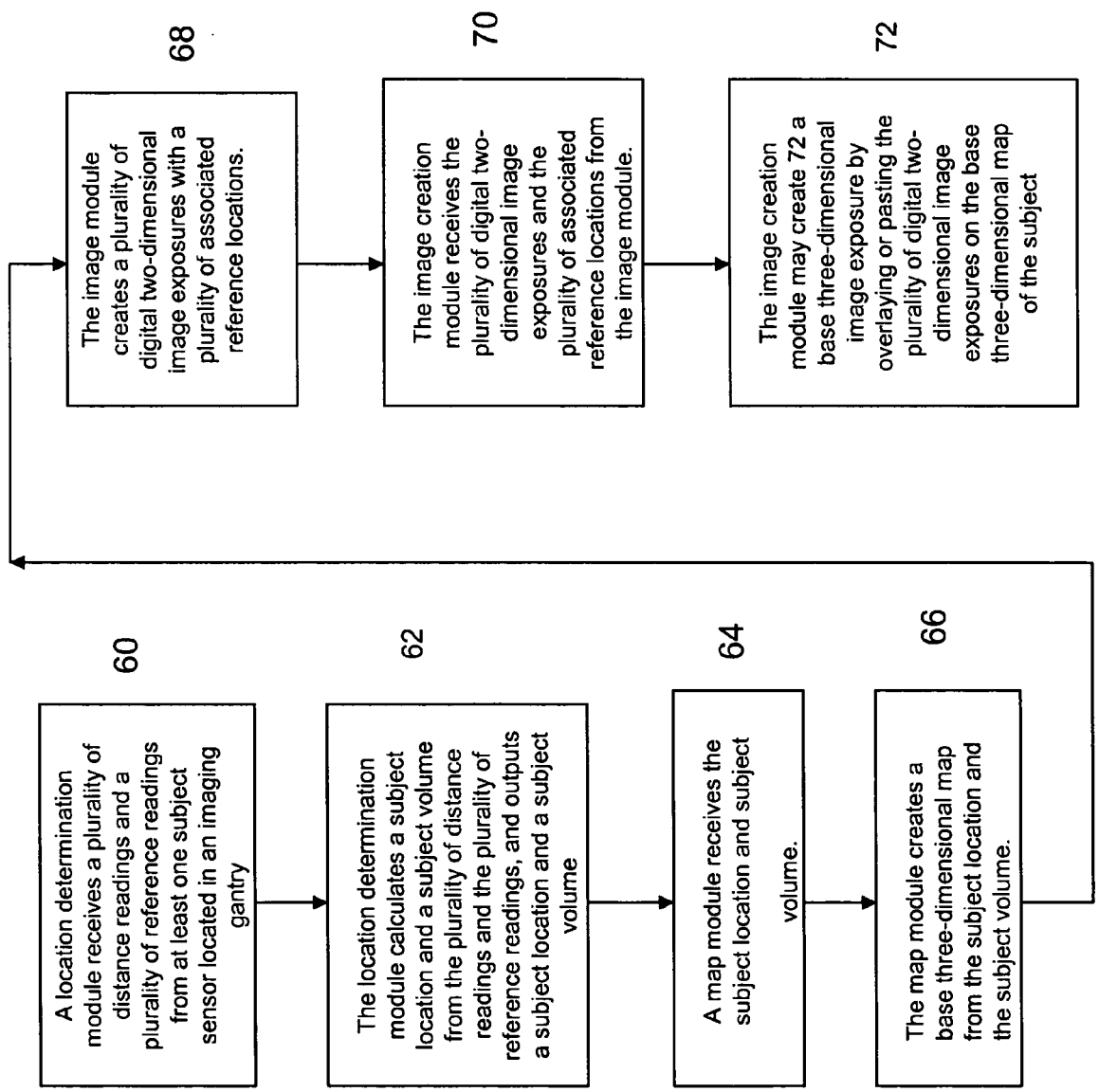
FIG. 10 illustrates a flowchart of the creation of a base three-dimensional image exposure according to an embodiment of the invention.

FIG. 10 illustrates a flowchart of the creation of a base three-dimensional image exposure according to an embodiment of the invention. A location determination module may receive 60 a plurality of distance readings and a plurality of reference readings from at least one subject sensor 12 located in an imaging gantry 10. The location determination module may calculate 62 a subject location and a subject volume, relative to at least one image source 14 and at least one image receptor 16, from the plurality of distance readings and the plurality of reference readings and output a subject location and a subject volume. A map module may receive 64 the subject location and the subject volume. The map module may create 66 a base three-dimensional map from the subject location and the subject volume. The image module may create 68 a plurality of digital two-dimensional image exposures with a plurality of associated reference locations by rotating at least one image source 14 and at least one image receptor 16 around the inner circumference of the imaging gantry 10 to create the plurality of two-dimensional image exposures and the plurality of associated reference locations and then digitizing the plurality of two-dimensional image exposures to create the plurality of digital two-dimensional image exposures. The image creation module may receive 70 the plurality of digital two-dimensional image exposures and the plurality of associated reference locations from the image module. The image creation module may create 72 a base three-dimensional image exposure by overlaying, interpolating, or pasting the plurality of digital two-dimensional image exposures on the base three-dimensional map of the subject, received from the map module, and by utilizing the associated reference information to determine where on the base three-dimensional map each of the plurality of digital two-dimensional image exposures are placed.

Figure 11:
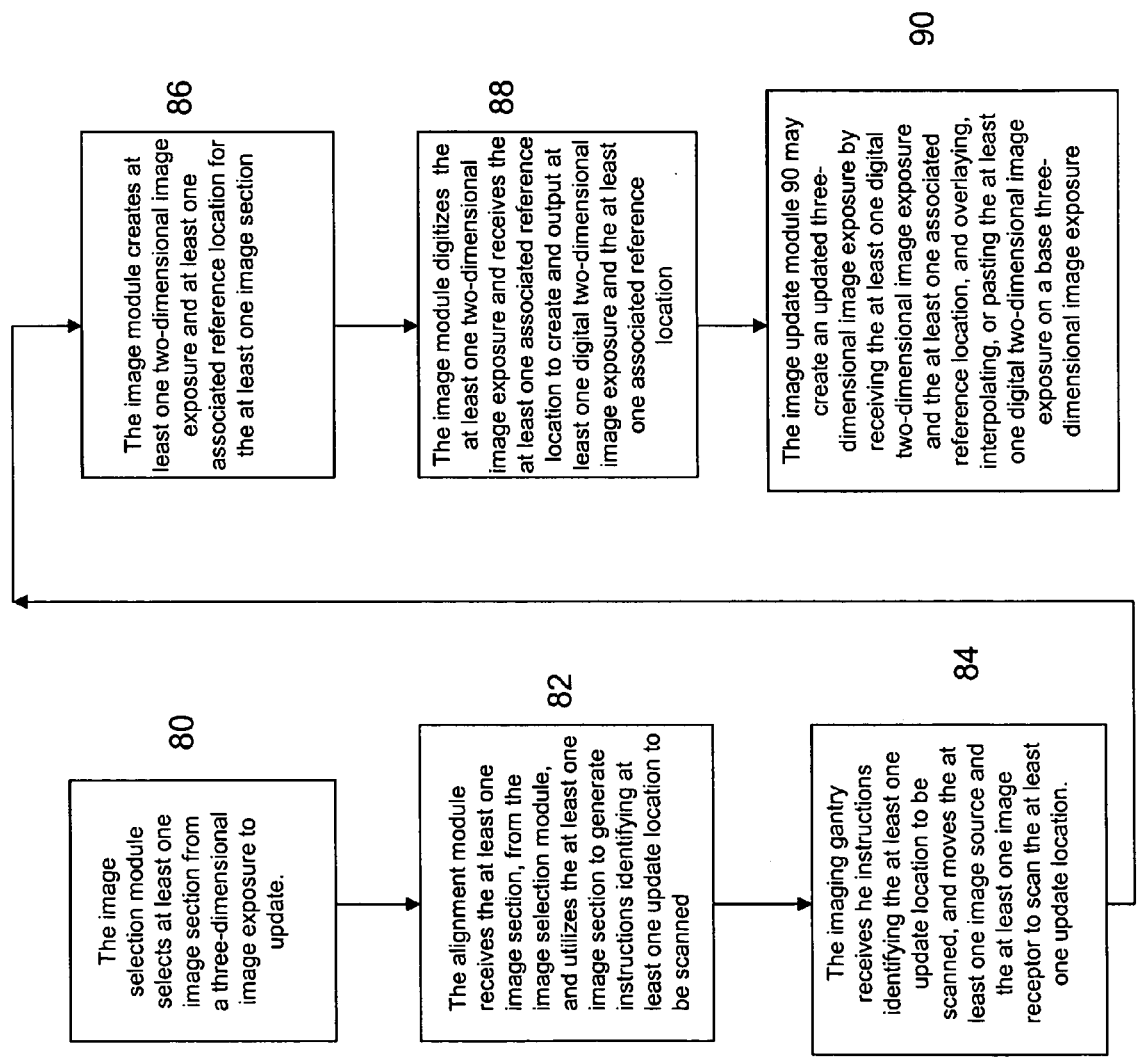
FIG. 11 illustrates a flowchart of the creation of an updated three-dimensional image exposure according to an embodiment of the invention.

FIG. 11 illustrates a flowchart of the creation of an updated three-dimensional image exposure according to an embodiment of the present invention. The image selection module may select 80 at least one image section from a three-dimensional image exposure to continuously update or to update in real time. The alignment module 82 may receive the at least one image section, from the image selection module, and utilize the at least one image section to generate instructions identifying at least one update location to be scanned. The imaging gantry 10 may receive 84 the instructions identifying the at least one update location to be scanned, and moves the at least one image source 14 and the at least one image receptor 16 to a start position in the imaging gantry that enables the at least one image source 14 and the at least one image receptor 16 to scan the at least one update location. The image module may create 86 at least one two-dimensional image exposure and at least one associated reference location for the at least one image section, by moving the at least one image source 14 and the at least one image receptor 16 around an inner circumference of the imaging gantry 10 to capture the at least one image section along with the at least one associated reference location. The image module may digitize 88 the at least one two-dimensional image exposure and receive the at least one associated reference location to create and output at least one digital two-dimensional image exposure and the at least one associated reference location. The image update module 90 may create an updated three-dimensional image exposure by receiving the at least one digital two-dimensional image exposure and the at least one associated reference location, and overlaying, interpolating, or pasting the at least one digital two-dimensional image exposure on a base three-dimensional image exposure utilizing the at least one associated reference location to indicate where on the base three-dimensional image exposure the at least one digital two-dimensional image exposure is placed.

Figure 12:
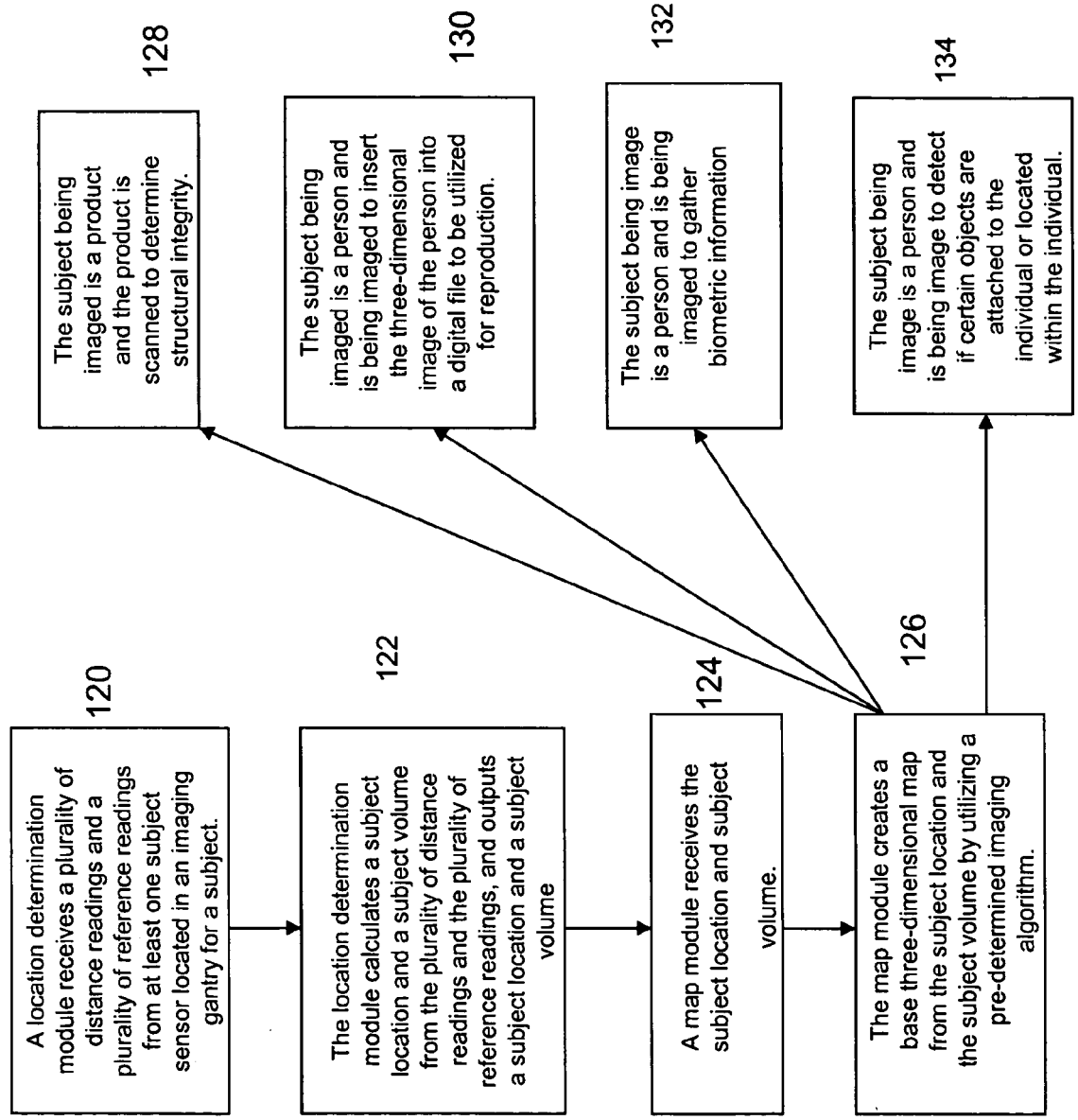
FIG. 12 illustrates a plurality of applications utilizing the three-dimensional imaging system according to an embodiment of the present invention.

FIG. 12 illustrates a plurality of applications utilizing the three-dimensional imaging system according to an embodiment of the present invention. A location determination module receives 120 a plurality of distance readings and a plurality of reference readings from at least one subject sensor located in an imaging gantry for a subject. The location determination module calculates 122 a subject location and a subject volume from the plurality of distance readings and the plurality of reference readings, and outputs a subject location and a subject volume. A map module receives 124 the subject location and subject volume. The map module creates 126 a base three-dimensional map from the subject location and the subject volume by utilizing a pre-determined imaging algorithm. The subject being imaged 128 is a product and the product is scanned to determine structural integrity. The subject being imaged 130 is a person and is being imaged to insert the three-dimensional image of the person into a digital file to be utilized for reproduction. The subject being image is a person 132 and is being imaged to gather biometric information. The subject being imaged 134 is a person and is being image to detect if certain objects are attached to the individual or located within the individual.

Figure 13:
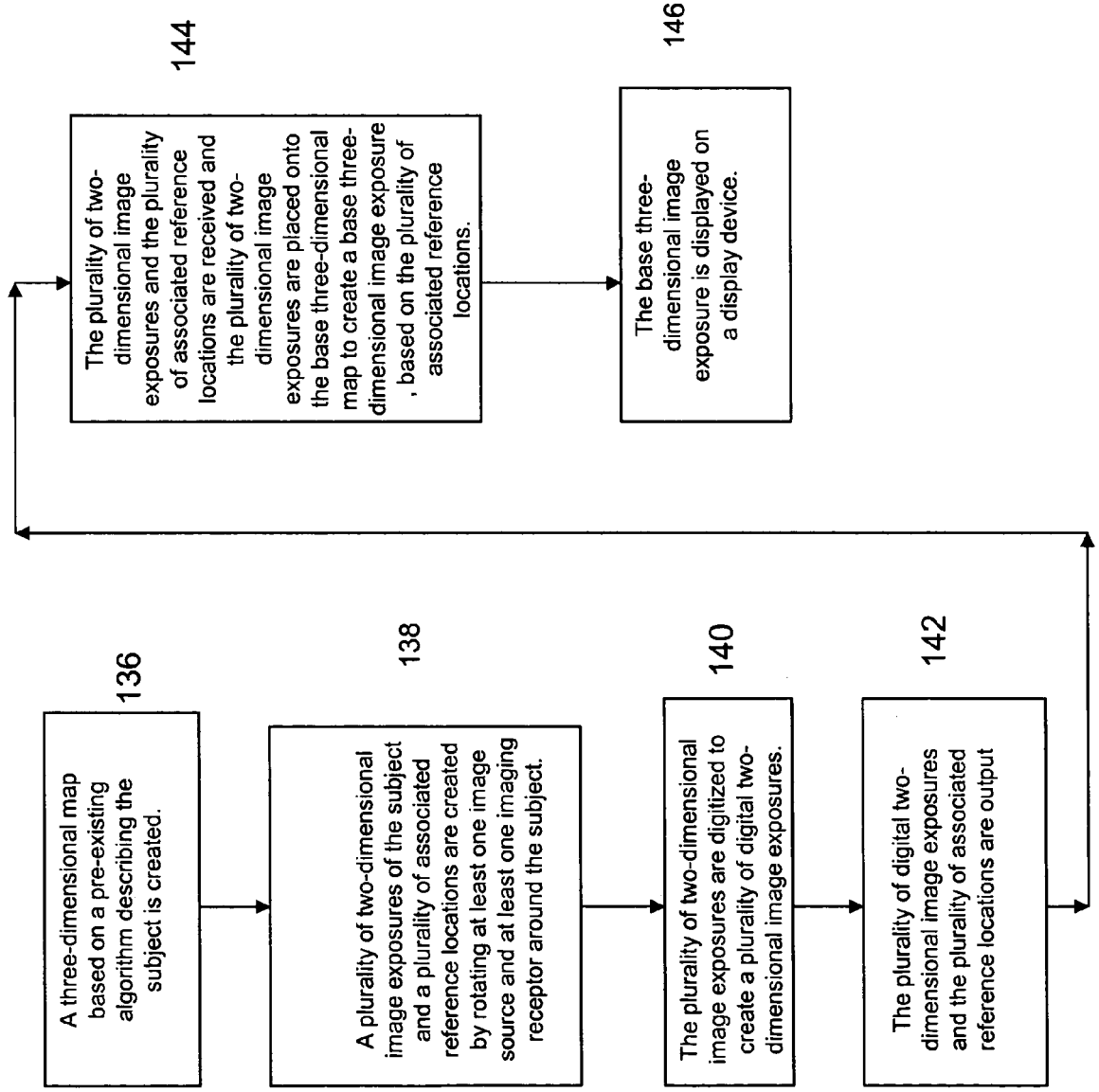
FIG. 13 illustrates an updating of a three-dimensional image when the base three-dimensional image is created using a pre-existing algorithm according to an embodiment of the invention.

FIG. 13 illustrates an updating of a three-dimensional image when the base three-dimensional image is created using a pre-existing algorithm according to an embodiment of the invention. A three-dimensional map based on a pre-existing algorithm describing the subject is created 136. A plurality of two-dimensional image exposures of the subject and a plurality of associated reference locations are created 138 by rotating at least one image source and at least one imaging receptor around the subject. The plurality of two-dimensional image exposures are digitized 140 to create a plurality of digital two-dimensional image exposures. The plurality of digital two-dimensional image exposures and the plurality of associated reference locations are output 142. The plurality of two-dimensional image exposures and the plurality of associated reference locations are received and the plurality of two-dimensional image exposures are placed 144 onto the base three-dimensional map to create a base three-dimensional image exposure. The base three-dimensional image exposure is displayed 146 on a display device, based on the plurality of associated reference locations.

In an embodiment of the invention, the plurality of two-dimensional image exposures are stored. In an embodiment of the invention, the plurality of digital two-dimensional image exposures are stored. The plurality of two-dimensional image exposures or the digital two-dimensional image exposures may be displayed on the display device. In an embodiment of the invention, a selected group of the stored digital two-dimensional image exposures or the two-dimensional image exposures may be displayed on the display device. In an embodiment of the invention, the two-dimensional image exposures or the plurality of digital two-dimensional image exposures may be displayed with the base three-dimensional image exposure. In an embodiment of the present invention, a portion of the plurality of digital or non-digital two-dimensional image exposures may be displayed with a portion of the base three-dimensional image exposure. In an embodiment of the invention, the portion of the base three-dimensional image exposures may be displayed on a display device.

Figure 14:
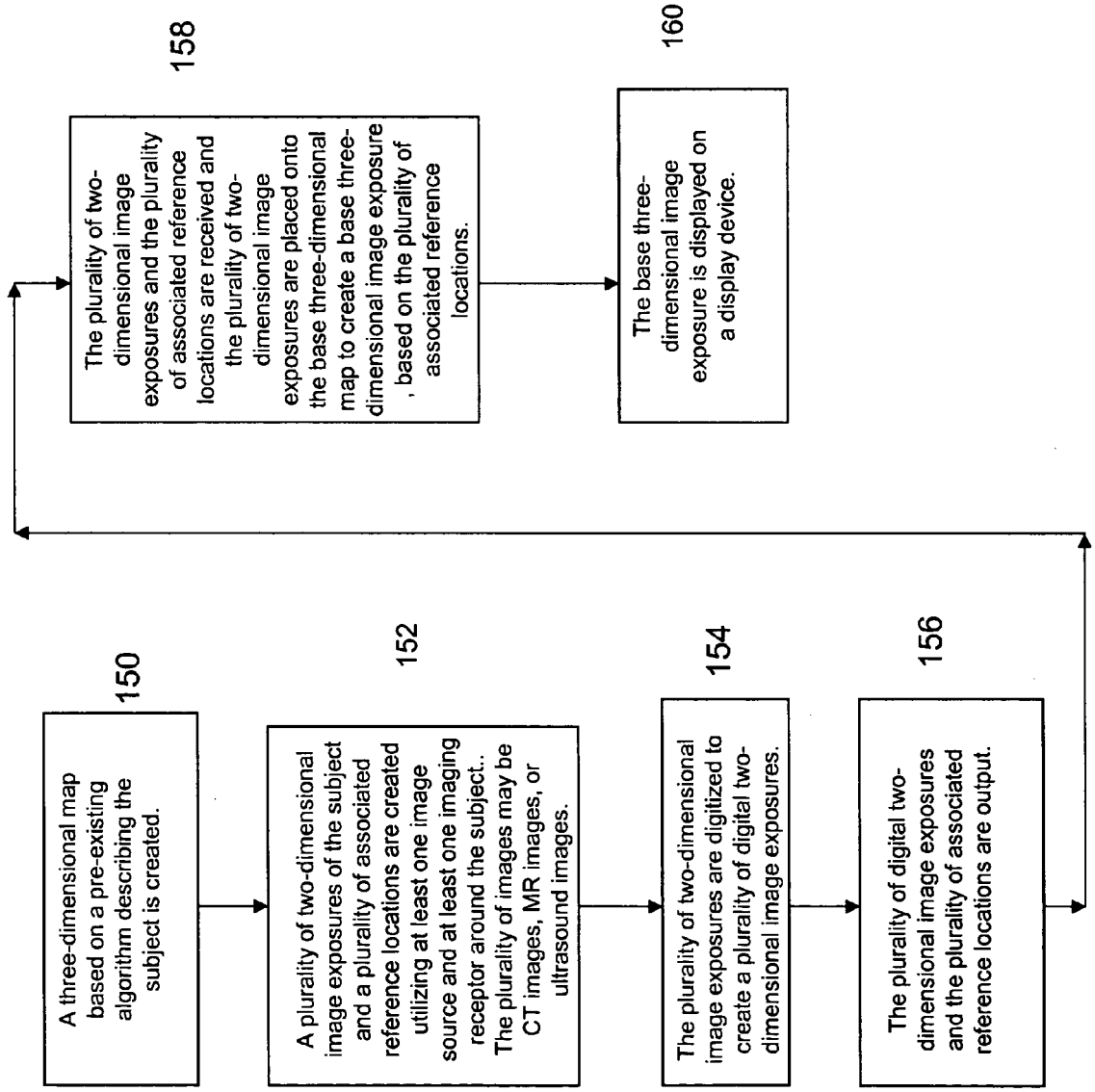
FIG. 14 illustrates an updating of a three-dimensional image where the image is a CT, MR, or Ultrasound image according to an embodiment of the present invention.

FIG. 14 illustrates an updating of a three-dimensional image where the image is a CT, MR, or Ultrasound image according to an embodiment of the present invention. A three-dimensional map based on a pre-existing algorithm describing the subject is created 150. A plurality of two-dimensional image exposures of the subject and a plurality of associated reference locations are created 152 utilizing at least one image source and at least one imaging receptor around the subject. The plurality of images may be CT images, MR images, or ultrasound images. The plurality of two-dimensional image exposures are digitized 154 to create a plurality of digital two-dimensional image exposures. The plurality of digital two-dimensional image exposures and the plurality of associated reference locations are output 156. The plurality of two-dimensional image exposures and the plurality of associated reference locations are received and the plurality of two-dimensional image exposures are placed onto the base three-dimensional map to create 158 a base three-dimensional image exposure, based on the plurality of associated reference locations. The base three-dimensional image exposure is displayed 160 on a display device.

FIG. 15 illustrates a creation of a three-dimensional image utilizing multiple collimation schemes according to an embodiment of the present invention. A three-dimensional map based on a pre-existing algorithm describing the subject is created 170. A plurality of two-dimensional image exposures of the subject and a plurality of associated reference locations are created 172 by rotating at least one image source and at least one imaging receptor around the subject. The plurality of two-dimensional image exposures are generated utilizing multiple collimation schemes. The plurality of two-dimensional image exposures are digitized to create 174 a plurality of digital two-dimensional image exposures. The plurality of digital two-dimensional image exposures and the plurality of associated reference locations are output 176. The plurality of two-dimensional image exposures and the plurality of associated reference locations are received and the plurality of two-dimensional image exposures are placed 178 onto the base three-dimensional map to create a base three-dimensional image exposure, based on the plurality of associated reference locations. The base three-dimensional image exposure is displayed 180 on a display device.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of creating a base-three dimensional image, comprising:
    receiving, at a location determination module, a plurality of distance readings and a plurality of reference readings for a subject from at least one subject sensor located in an imaging gantry, the at least one subject sensor located within the imaging gantry to provide the plurality of distance readings and the plurality of reference readings;
    calculating a subject location and a subject volume, relative to at least one image source and at least one image receptor, from the plurality of distance readings and the plurality of reference readings, and output the subject location and the subject volume;
    receiving, at a map module, the subject location and the subject volume; and
    creating, at the map module, a base three-dimensional map from the subject location and the subject volume by utilizing a pre-determined imaging algorithm.

2. The method of claim 1, wherein the subject to be scanned is a product, and the imaging gantry is imaging the product to determine structural integrity of the product.

3. The method of claim 1, wherein the subject to be scanned is an individual and the imaging gantry is imaging the person to insert an image of the person into a digital file to be utilized as a reproduction of the person.

4. The method of claim 1, wherein the subject to be scanned is an individual and the imaging gantry is imaging the individual to detect if certain objects are attached to the individual or located within the individual.

5. The method of claim 1, wherein the subject to be scanned is an individual and the imaging gantry is imaging the individual to gather biometric information which is utilized to identify the individual.

6. The method of claim 1, wherein the map module includes pre-existing subject location and subject volume information which is used in combination with the subject location and the subject volume to create the base three-dimensional map.

7. A method of creating an updating three-dimensional image exposure of a subject in an imaging gantry, comprising:
    creating a base three-dimensional map based on a preexisting algorithm describing the subject;
    creating a plurality of two-dimensional image exposures of the subject and a plurality of associated reference locations by rotating at least one image source and at least one image receptor around the subject; and
    digitizing the plurality of two-dimensional image exposures to create a plurality of digital two-dimensional image exposures;
    outputting the plurality of digital two-dimensional image exposures and the plurality of associated reference locations;
    receiving the plurality of two-dimensional image exposures and the plurality of associated reference locations and placing the plurality of two-dimensional image exposures onto the base three-dimensional map to create a base three-dimensional image exposure, the placing of the plurality of two-dimensional image exposures determined by the plurality of associated reference locations; and
    displaying the base three-dimensional image exposure on a display device.

8. The method of claim 7, further including utilizing stored pre-existing geometrical calculations regarding the subject to assist in creating the base three-dimensional map.

9. The method of claim 7, further including utilizing stored pre-existing mathematical functions regarding the subject to assist in creating the base three-dimensional map.

10. The method of claim 7, wherein an inner circumference of the imaging gantry is rotated about the subject to rotate the at least one image source and the at least one image receptor around the subject.

11. The method of claim 7, wherein the imaging gantry is rotated about the subject to rotate the at least one image source and the at least one image receptor around the subject.

12. The method of claim 7, wherein a number of image receptors is larger than a number of image sources.

13. The method of claim 7, wherein a number of images sources is larger than a number of image receptors.

14. The method of claim 7, wherein the at least one image receptor and the at least one image source move synchronously with respect to each other.

15. The method of claim 7, wherein the at least one image receptor and the at least one image source move asynchronously with respect to each other.

16. The method of claim 7, wherein the at least one image receptor and the at least one image source are offset with respect to each other and not directly opposite to each other.

17. The method of claim 7, further including storing the plurality of two-dimensional image exposures.

18. The method of claim 17, further including displaying of the stored plurality of two-dimensional image exposures.

19. The method of claim 17, further including displaying a selected group of the stored plurality of two-dimensional image exposures.

20. The method of claim 19, further including displaying a portion of the three-dimensional image exposure in addition to the selected group of the stored plurality of two-dimensional image exposures.

21. The method of claim 7, further including displaying only a portion of the three-dimensional image exposure.

22. A method of creating an updating three-dimensional image exposure of a subject in an imaging gantry, comprising:

creating a base three-dimensional map based on a preexisting algorithm describing the subject;

creating a plurality of two-dimensional image exposures of the subject and a plurality of associated reference locations utilizing at least one image source and at least one image receptor; and digitizing the plurality of two-dimensional image exposures to create a plurality of digital two-dimensional image exposures;

outputting the plurality of digital two-dimensional image exposures and the plurality of associated reference locations;

receiving the plurality of two-dimensional image exposures and the plurality of associated reference locations and placing the plurality of two-dimensional image exposures onto the base three-dimensional map to create a base three-dimensional image exposure, the placing of the plurality of two-dimensional image exposures determined by the plurality of associated reference locations; and displaying the base three-dimensional image exposure on a display device.

23. The method of claim 22, wherein a fulcrom is utilized to generate a plurality of computerized tomography (CT) images and the plurality of CT images are utilized as the plurality of two dimensional image exposures.

24. The method of claim 22, wherein a fulcrom is utilized to generate a plurality of magnetic resonance (MR) images and the plurality of MR images are utilized as the plurality of two dimensional image exposures.

25. The method of claim 22, wherein the at least one image source and the at least one image sensor are ultrasound image sensors and the plurality of two-dimensional image exposures are a plurality of ultrasound two-dimensional image exposures.

26. A method of creating an updating three-dimensional image exposure of a subject in an imaging gantry, comprising:

creating a base three-dimensional map based on a preexisting algorithm describing the subject;

creating a plurality of two-dimensional image exposures of the subject and a plurality of associated reference locations by rotating at least one image source and at least one image receptor around the subject; and digitizing the plurality of two-dimensional image exposures to create a plurality of digital two-dimensional image exposures;

outputting the plurality of digital two-dimensional image exposures and the plurality of associated reference locations;

receiving the plurality of two-dimensional image exposures and the plurality of associated reference locations and placing the plurality of two-dimensional image exposures onto the base three-dimensional map to create a base three-dimensional image exposure, the placing of the plurality of two-dimensional image exposures determined by the plurality of associated reference locations; and displaying the base three-dimensional image exposure on a display device, wherein multiple collimation schemes are utilized to create the plurality of two-dimensional image exposures.

27. The method of claim 26, wherein the multiple collimation schemes are selected from a group of cone beam, fan beam, and focused beam.

* * * * *